United States Patent
Deabes et al.

(10) Patent No.: US 10,041,899 B2
(45) Date of Patent: Aug. 7, 2018

(54) PORTABLE ELECTRICAL CAPACITIVE TOMOGRAPHY IMAGING DEVICE AND METHOD OF OPERATION

(71) Applicant: Umm Al-Qura University, Makkah (SA)

(72) Inventors: Wael Deabes, Makkah (SA); Majid Saeed Almaraashi, Makkah (SA)

(73) Assignee: Umm Al-Qura University, Makkah (SA)

( * ) Notice: Subject to any disclaimer, the term of this patent is extended or adjusted under 35 U.S.C. 154(b) by 338 days.

(21) Appl. No.: 15/060,246

(22) Filed: Mar. 3, 2016

(65) Prior Publication Data
US 2017/0254768 A1 Sep. 7, 2017

(51) Int. Cl.
G01N 27/22 (2006.01)

(52) U.S. Cl.
CPC ......... G01N 27/221 (2013.01); G01N 27/226 (2013.01)

(58) Field of Classification Search
CPC .. G01N 27/221; G01N 27/228; G01N 27/226; G01N 27/223; G01N 27/904; G01N 33/0031; G01N 33/0062
See application file for complete search history.

(56) References Cited

U.S. PATENT DOCUMENTS

| | | | |
|---|---|---|---|
| 6,697,508 B2 * | 2/2004 | Nelson | G06T 11/006 378/4 |
| 7,496,450 B2 | 2/2009 | Ortiz Aleman et al. | |
| 8,855,947 B2 * | 10/2014 | Sheila-Vadde | G01F 1/66 702/49 |
| 2007/0133746 A1 * | 6/2007 | Ortiz Aleman | G01F 1/64 378/59 |
| 2012/0038368 A1 * | 2/2012 | Mahalingam | A61B 5/0536 324/603 |
| 2012/0177274 A1 * | 7/2012 | Koehler | G06T 5/50 382/131 |

FOREIGN PATENT DOCUMENTS

| | | |
|---|---|---|
| CN | 1538168 A | 10/2004 |
| EP | 2182333 A1 | 5/2010 |

OTHER PUBLICATIONS

Chun, S., et al., "Diagnostic Flow Metering using Ultrasound Tomography", Journal of Mechanical Science and Technology, vol. 25, No. 6, pp. 1475-1482, (2011).

(Continued)

*Primary Examiner* — Jaehwan Oh
(74) *Attorney, Agent, or Firm* — Oblon, McClelland, Maier & Neustadt, L.L.P.

(57) ABSTRACT

An Electrical Capacitive Tomography (ECT) sensor system for imaging heterogeneous dielectric material includes multiple ECT sensor heads, a portable, wireless ECT reader that interfaces with the ECT sensor heads. The ECT reader includes an efficient low computational cost fuzzy logic dielectric ECT image synthesizer. The fuzzy logic dielectric ECT image synthesizer can an independent processing chain for each pixel. Due to the low computation cost the fuzzy logic image synthesizer is able to produce video imagery of dynamic flows or reactions.

22 Claims, 16 Drawing Sheets

(56) References Cited

OTHER PUBLICATIONS

Deabes, W.A., et al., "A Wide Frequency Range Circuit for Measuring Mutual Capacitance with Application to Monitoring of Metal Fill Profile", Institute of Electrical and Electronics Engineers, pp. 362-367, (2008).

Deabes, W.A., et al., "Analysis, Design and Application of a Capacitance Measurement Circuit with Wide Operating Frequency Range", 17th IEEE International Conference on Control Applications, pp. 114-119, (2008).

Deabes, W., et al., "A New Wide Frequency Band Capacitance Transducer with Application to Measuring Metal Fill Time", Sensors & Transducers Journal, vol. 100, No. 1, pp. 72-84, (Jan. 2009).

* cited by examiner

500

600

FUZZY INPUT-OUTPUT ACTIVATION GRAPHS

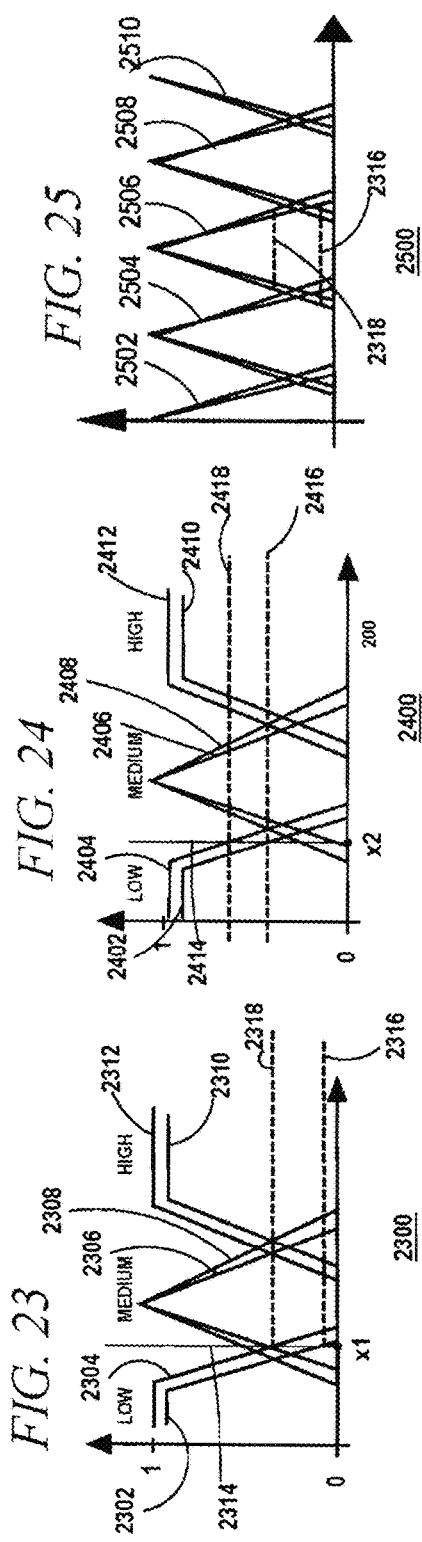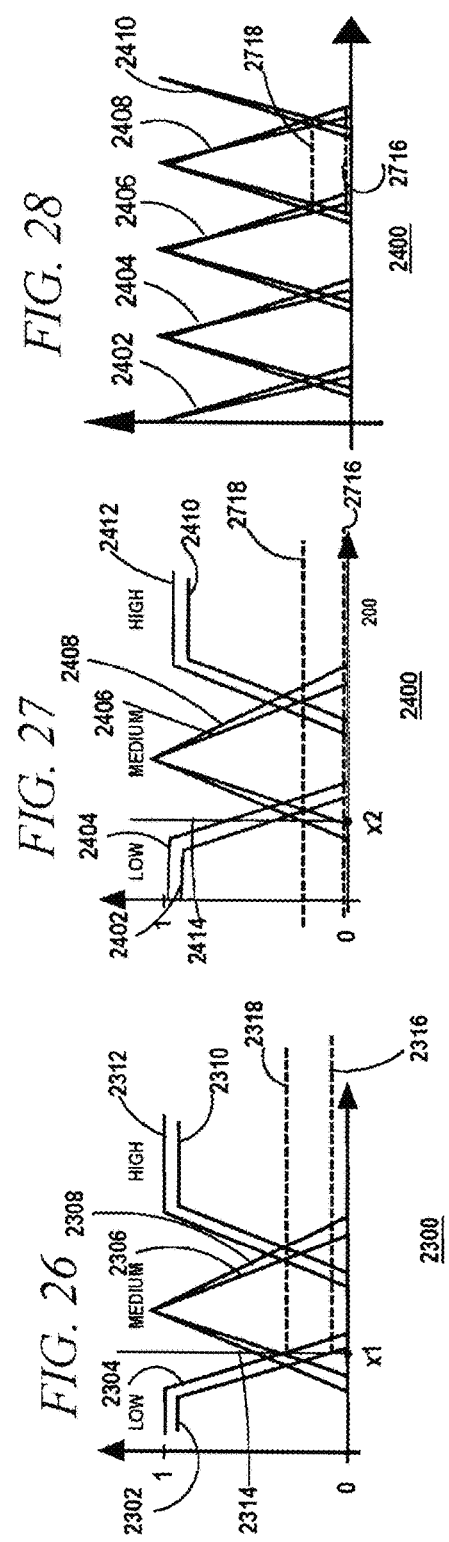

PORTABLE ELECTRICAL CAPACITIVE TOMOGRAPHY IMAGING DEVICE AND METHOD OF OPERATION

FIELD OF THE DISCLOSURE

The present disclosure is related to Electrical Capacitive Tomography (ECT) systems.

BACKGROUND

Many different types of industrial processes and machines handle heterogeneous materials. A heterogeneous material can be a mixed phased material. A mixed phase material includes two or more states of matter, e.g., two or more of liquid, gas, and solid materials. In some cases all three states of matter may be present. A heterogeneous material can also include two immiscible materials of the same phase, for example, oil and water. Examples of processing involving heterogeneous materials include coal gasifiers, carbon capture processes, combustion chambers, and Fischer-Tropsch synthesis, wet gas separators, pneumatic conveyors, cyclone separators, fluidised beds and fluidised bed dryers, batch mixing, slurry (or hydraulic) conveying, oil refining, oil drilling, pipe line transport. It would be desirable for many purposes such as process control and process optimization to be able to obtain a 3-D image as well as 2-D cross sectional images of heterogeneous materials in such industrial processes. X-ray computed tomography would generally be too slow and prohibitively expensive for most industrial processes.

Electrical Capacitive Tomography (ECT) scanning has been used to obtain 2-D cross sectional images. However for the most part, ECT systems rely on time consuming and computationally intensive algorithms that involve iteratively recomputing electrostatic field solutions. Such iterative solutions are too slow for real time imaging of rapidly changing multi-phase flows and processing unless computer hardware that is cost prohibitive were to be used.

In many industrial settings such as in oil refineries or oil pipelines, it would be desirable to have multiple ECT sensors installed. For example ECT sensors can be installed on different equipment in an oil refinery to monitor different stages of an oil refining process. In the case of an oil pipline, it would be desirable to have ECT sensors installed at multiple locations on the pipeline feeding into within pumping stations, so as to obtain advance warning of any undesirable flow attributes such as for example a slug of gas or oil approaching the pumping station.

Due to the design of any given industrial plant at which it is desirable to install one or more ECT sensors, the location of the pipe section or processing chamber on which it is desired to place a monitoring ECT sensor may be inaccessible on a day-to-day basis due to safety considerations or due to the physical location. Furthermore, due to hazardous environmental conditions in certain types of facilities, that include heat and hot vapors, certain sensitive electronics used in an ECT imaging device will have an unacceptably short lifetime.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

SUMMARY

The present disclosure describes an ECT system that includes multiple ECT sensor heads, and a portable, wireless ECT imaging and sensor head reading device (referred to herein below as the "ECT reader") that can wirelessly interface with each of the multiple installed ECT sensor heads. Because the ECT reader is portable it need not be permanently installed within a plant or outside in harsh conditions (e.g., in desert or sub-arctic pipeline locations) where conditions would tend to rapidly break down the electronics. The ECT reader includes a fuzzy logic ECT dielectric imaging system that is capable of imaging multi-phase dielectric material. In contrast to other approaches, the fuzzy logic ECT dielectric imaging system, in one example, is not an iterative method and has a much lower computational cost than iterative approaches, which in some cases require hundreds of iterations to produce an image. Due to the low computational cost of the fuzzy logic ECT dielectric imaging system, the energy requirements for imaging are significantly lower than when relying on traditional techniques, so that an easily portable, handheld ECT reader can be provided. The ECT reader can weigh less than 1 Kg and thus is not burdensome to carried about by facility workers so they can have the device at the ready and can wirelessly interface it with any sensor head in a facility in order to obtain an 2-D cross-sectional images of 3-D volume imagery of multiphase dielectric contents of any processing chamber or conduit.

According to certain embodiments a Field Programmable Gate Array (FPGA) is used to implement fuzzy logic ECT imaging and other functions of the ECT reader and to produce images from input ECT measurements.

According to certain embodiments the FPGA is configured to have a separate processing chain for each pixel of an ECT image being generated from the ECT data.

According to certain embodiments the separate processing chains operate concurrently in parallel to produce the ECT image. This affords rapid image generation and therefore, in certain, embodiments by using an FPGA to implement the disclosed fuzzy logic ECT image reconstruction a relatively high frame rate (e.g., 300 or more frames per second) ECT video can be obtained. A high frame rate is important to keep pace with a rapid mixed phase flow in a conduit, or to keep pace with highly dynamic mixed phase contents of a chemical reactor.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 23 is a graph including plots of type-2 fuzzy logic membership functions representing low, medium and high levels of noise according to one example;

FIG. 24 is a graph including plots of type-2 fuzzy logic membership functions representing low, medium and high counts of FEM elements according to one example;

FIG. 25 is a graph including type-2 fuzzy logic output membership functions;

FIG. 26 is a duplicate of FIG. 23 which is shown to illustrate evaluation of a different fuzzy logic conditional statement according to one example;

FIG. 27 is a duplicate of FIG. 24 which is shown to illustrate evaluation of a different fuzzy logic conditional statement according to one example;

FIG. 28 is a duplicate of FIG. 25 which is shown to illustrate evaluation of a different fuzzy logic conditional statement according to one example;

DETAILED DESCRIPTION OF THE EMBODIMENTS

Figure 1:
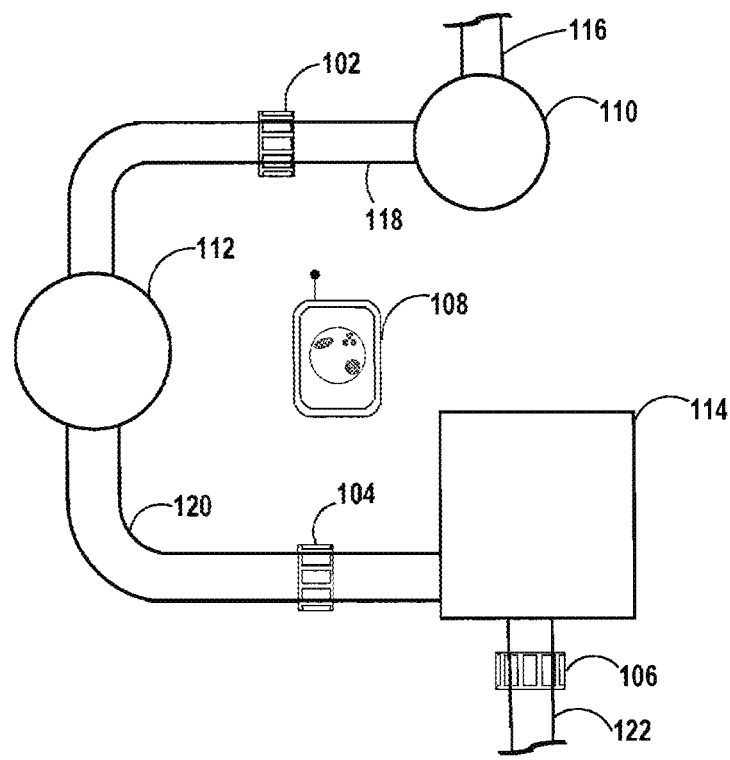
FIG. 1 is depiction of a generic heterogeneous dielectric material processing facility that includes multiple Electrical Capacitive Tomography (ECT) sensor heads and an ECT reader according to one example.

Referring now to the drawings, wherein like reference numerals designate identical or corresponding parts throughout the several views.

FIG. 1 is depiction of a generic heterogeneous dielectric material processing facility 100 that includes multiple Electrical Capacitive Tomography (ECT) sensor heads. For instance, as shown in FIG. 1, the processing facility includes a first ECT sensor head 102, a second ECT sensor head 104, a third ECT sensor head 106, and an ECT reader 108. The facility can be a type of facility that process heterogeneous dielectric materials such as, by way of non limited example, a coal gasifier facility, a carbon capture facility, a combustion facility, a facility for carrying Fischer-Tropsch reactions on an industrial scale, a wet gas separator facility, a facility with pneumatic conveyors, a facility with cyclone separators, a facility including fluidised beds and/or fluidised bed dryers, a facility for batch mixing, a facility including slurry (or hydraulic) conveying, an oil refining facility, an oil drilling facility or a pipe line transport facility.

The facility 100 includes three heterogeneous dielectric material processing stations. For instance, the facility 100 includes a first heterogeneous dielectric material processing station 110, a second heterogeneous dielectric material processing station 112, and a third heterogeneous dielectric material processing station 114. It must be appreciated that the facility 100 may alternatively include a different number of processing stations than that shown in FIG. 1.

An inlet heterogeneous dielectric material conduit 116 leads into the first processing station 110. The first processing station 110 is connected to the second processing station 112 through a second heterogeneous dielectric material conduit 118. The second processing station 112 is connected to the third processing station 114 through a third heterogeneous dielectric material conduit 120. An outflow heterogeneous dielectric material conduit 122 leads out of the third processing station 114. The first ECT sensor head 102 is disposed about the second heterogeneous dielectric material conduit 118, the second ECT sensor head 104 is disposed about the third heterogeneous dielectric material conduit 120, and the third ECT sensor head 106 is disposed about the outflow heterogeneous dielectric material conduit 122.

The facility 100 can be large, for example spread out over 10,000 square meters or more, and in practice can include a greater number of material processing stations, conduits, and ECT sensor heads. The facility may be outdoors and subject to a harsh climate (e.g., desert, or subarctic conditions). Thus, it would be burdensome for personnel working at larger facilities to carry around a computer having sufficient computational processing power to execute the computationally intensive iterative ECT image reconstruction algorithms in real time.

In contrast, as described herein an ECT reader 108 can implement a low computational cost direct (single iteration) fuzzy logic ECT dielectric imaging system. As a practical matter, one would like the ECT reader 108 to be able to operate for an entire work shift of 8 to 12 hours. Ideally it would be desirable for the ECT reader 108 to operate for two work shifts totaling 16 hours. The low computational cost of the fuzzy logic ECT dielectric imaging system described herein below reduces the size of the battery that is needed for one or two shift continuous operation and thus reduces the resulting weight of the ECT reader 108, thereby allowing the reader to be carried about all day by facility technicians without being too burdensome.

The ECT reader 108 can use a Field Programmable Gate Array (FPGA) to implement the fuzzy logic ECT dielectric imaging system. For example in the case of the example described later with reference to FIG. 20, the FPGA can include a separate processing chain for each pixel of output image produced from data that is obtained from the ECT sensor heads 102, 104, 106. Providing a separate processing chain for each pixel allows the ECT reader 108 to produce images at high frame rates so that a video of multiphase flow in the conduits 118, 120, 122 can be displayed. A high frame rate is important when imaging high speed multi-phase flows.

Figure 2:
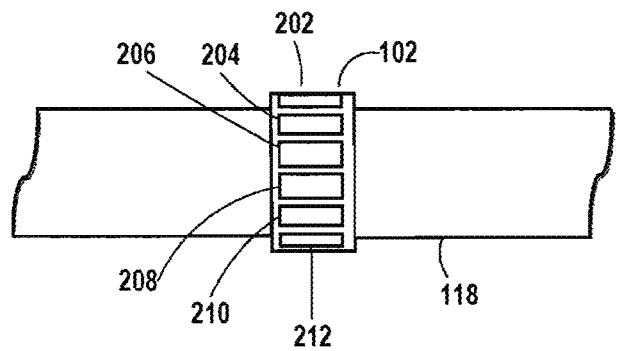
FIG. 2 is a side view of a conduit fitted with an ECT sensor head according to one example.

FIG. 2 is a side view of the second heterogeneous dielectric material conduit 118 fitted with the first ECT sensor head 102. The first ECT sensor head 102 includes a set of twelve sensing electrodes including a first sensing electrode 202, a second sensing electrode 204, a third sensing electrode 206, a fourth sensing electrode 208, a fifth sensing electrode 210, a sixth sensing electrode 212, and shown in FIG. 3 a seventh sensing electrode 302, an eighth sensing electrode 304, a ninth sensing electrode 306, a tenth sensing electrode 308, an eleventh sensing electrode 310 and a twelfth sensing electrode 312 proximate to the conduit 118 and spaced about its periphery (circumference) 214.

Figure 3:
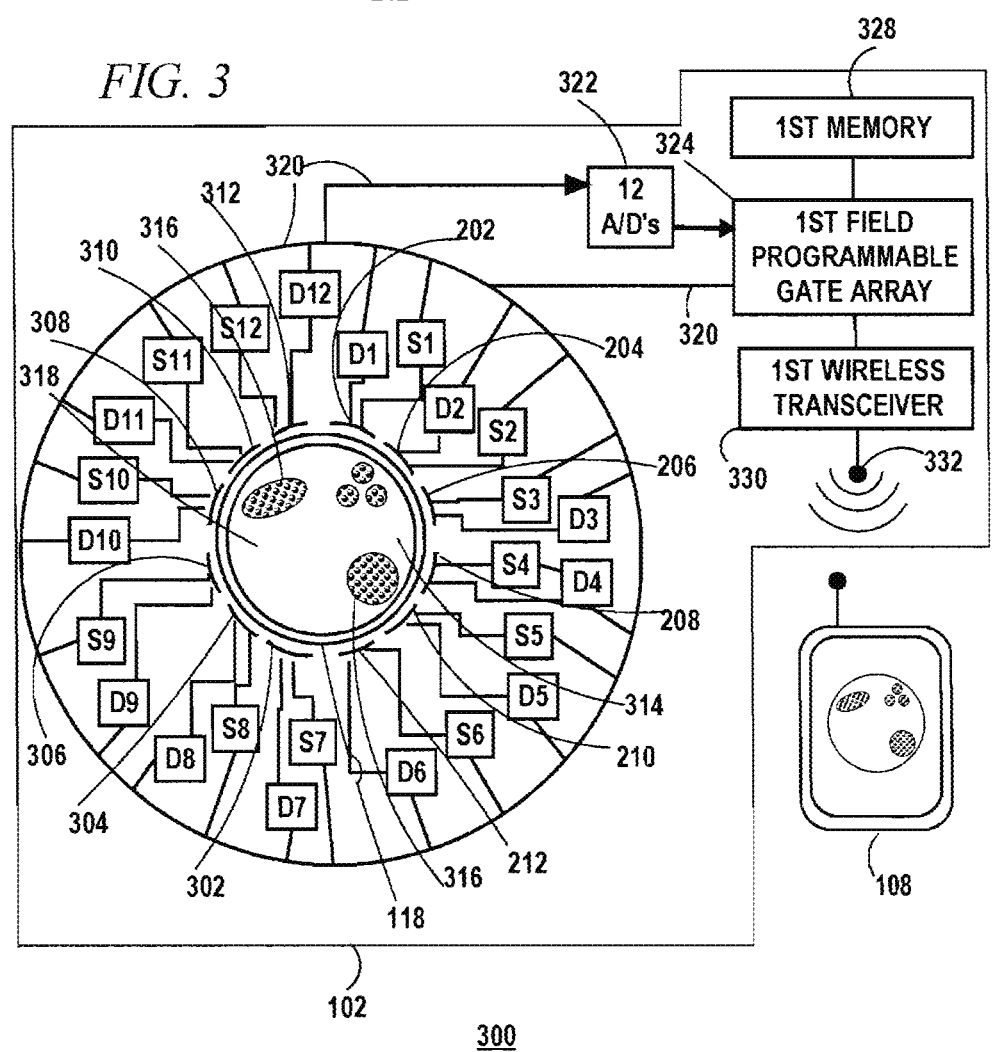
FIG. 3 is a schematic cross sectional view of an ECT sensor head shown in FIG. 2 along with a block diagram representation of electronics of the sensor head and an ECT reader that interfaces wirelessly with the electronics of the ECT sensor head according to one example.
Figure 22:
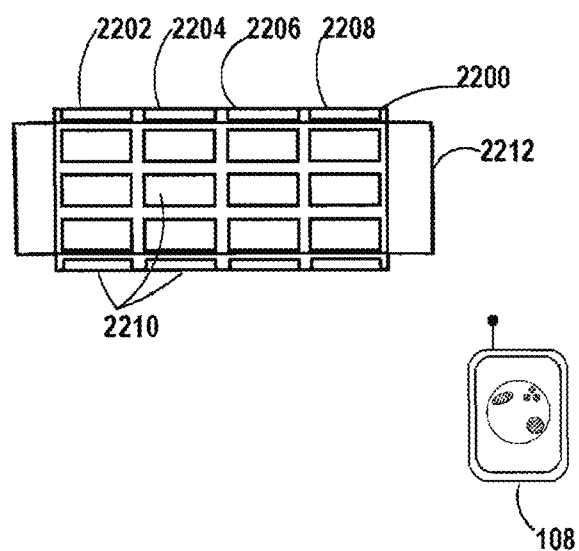
FIG. 22 is a side view of an ECT sensor head that has multiple axially spaced rings of electrodes and an ECT reader according to one example.
Figure 29:
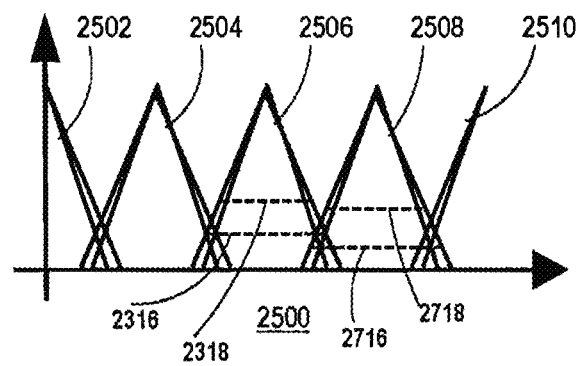
FIG. 29 illustrates a process of defuzzifying output membership functions that are output by two conditional fuzzy logic rules, which are illustrated with reference to FIGS. 23-28 according to one example.

The teachings of the present disclosure can be applied to ECT sensor heads having variations on the numbers of electrodes, electrode geometry, electrode arrangement, and pipe geometry relative to what is shown in FIGS. 1-3. The sensor head 102 shown in FIGS. 1-3 includes a single circular array of electrodes and is suitable for obtaining a 2-D cross sectional image of the heterogeneous dielectric flow in the conduit 118. Arrangements with multiple rings of electrodes as shown in FIG. 22 are suitable for obtaining 3-D images of heterogeneous dielectric materials. The other ECT sensor heads, e.g., the second sensor head 104 and the third sensor head 106 can have the same design as shown in FIGS. 2-3 or a different design.

FIG. 3 is a schematic cross-sectional view of the first ECT sensor head 102 shown in FIG. 2 along with a block diagram representation of electronics of the sensor head 102 and the ECT reader 108 that interfaces wirelessly with the electronics of the first ECT sensor head 102. Taken together the ECT sensor head 102 and the ECT reader 108 form an ECT sensor system 300. As shown in FIG. 3, the second conduit 118 has within it a heterogeneous dielectric material 314 that includes a first material (e.g., gas) 316 and a second material 318 (e.g., oil). First through twelfth signal generator circuits S1-S12 are connected respectively to the first through twelfth sensing electrodes 202, 204, 206, 208, 210, 212, 302, 304, 306, 308, 310, 312. The signal generator circuits S1-S12 can for example include square wave generators, sinusoidal signal generators, or generators of any other waveforms. Also, first through twelfth signal detector circuits D1-D12 are connected respectively to the first through twelfth sensing electrodes 202, 204, 206, 208, 210, 212, 302, 304, 306, 308, 310, 312. The signal detector circuits D1-D12 can for example include lock in amplifiers.

In operation, each of the signal generators S1-S12 is turned on and the signal detector circuits D1-D12 not associated with the same sensing electrode as the signal generator that was turned on are activated in order to sense the signal produced by the signal generator that was turned on. A signal produced by one of the signal generators S1-S12 is transferred between a pair of the sensing electrodes 202, 204, 206, 208, 210, 212, 302, 304, 306, 308, 310, 312 according to their mutual capacitance. The total number of independent mutual capacitance measurements that can be obtained between N sensing electrodes is $N*(N-1)/2$. For the embodiment shown in FIG. 3 in which the number of independent sensing electrodes is 12, the number of mutual capacitance measurements that can be obtained is equal to 66.

The mutual capacitance between a given pair of sensing electrodes is dependent on the geometry of the sensing electrodes and the relative positioning of sensing electrodes both of which are known. Further, the mutual capacitance is also dependent on the spatial distribution of the constituents 316, 318 of the heterogeneous dielectric material 314 within the conduit 118, as each constituent has a different dielectric constant. The function of the ECT sensor system 300 is to form an image of the distribution of the constituents 316, 318 of the heterogeneous dielectric material 314. However, doing so is an ill posed inverse problem and increasingly so when a higher resolution is being sought. For instance, the problem is an ill posed inverse problem when a relatively low resolution of 16 by 16 pixel image is to be produced. A 16 by 16 image has a total of 256 pixels and the first ECT sensor head 102 has 12 electrodes between which 66 mutual capacitance measurements can be taken. It is apparent that the number of pixels exceeds the number of measurements by nearly a factor of 4. It should also be noted that capacitance measurements are not fully independent in the sense that a change in the dielectric of a particular pixel can affect more than one of the mutual capacitance measurements. Additionally, changes in the dielectric constant of many different pixels can affect each mutual capacitance measurement, equally or similarly thereby making it problematic to determine the dielectric constant of a particular pixel.

A signal bus 320 connects to the signal generators S1-S12 and to the signal detector circuits D1-D12. Outputs of the detector circuits D1-D12 are coupled through the signal bus 320 to analog inputs of a set of 12 Analog-to-Digital converters (A/Ds) 322. The signals that are input to the A/Ds 322 are proportional to the mutual capacitance between combinations (e.g., out of the 66 combinations) of the sensing electrodes 202, 204, 206, 208, 210, 212, 302, 304, 306, 308, 310, 312. Digital outputs of the A/Ds 322 are coupled to a first Field Programmable Gate Array (FPGA) 324. The first FPGA 324 is coupled through the signal bus 320 to the signal generator circuits S1-S12. The first FPGA 324 transmits control signals through the signal bus to the signal generator circuits S1-S12, in order to selectively activate the signal generator circuits S1-S12.

A first memory 328 is coupled to the first FPGA 324. The first memory 328 stores a configuration for the first FPGA 324. A first wireless transceiver 330 equipped with a first antenna 332 is coupled to the first FPGA 324. The configuration stored in the first memory 328 configures the first FPGA 324 to collect mutual capacitance measurements between the sensing electrodes 202, 204, 206, 208, 210, 212, 302, 304, 306, 308, 310, 312 that are obtained using the signal generator circuits S1-S12 and the signal detector circuits D1-D12. The capacitive measurements are digitized by the 12 A/Ds 322 and further transmitted using the first wireless transceiver 330 and via the first antenna 332 to the ECT reader 108. The signal bus 320, A/Ds 322, the first FPGA 324, the first memory 326, and the first wireless transceiver 330 are embodied in electrical circuitry.

Figure 4:
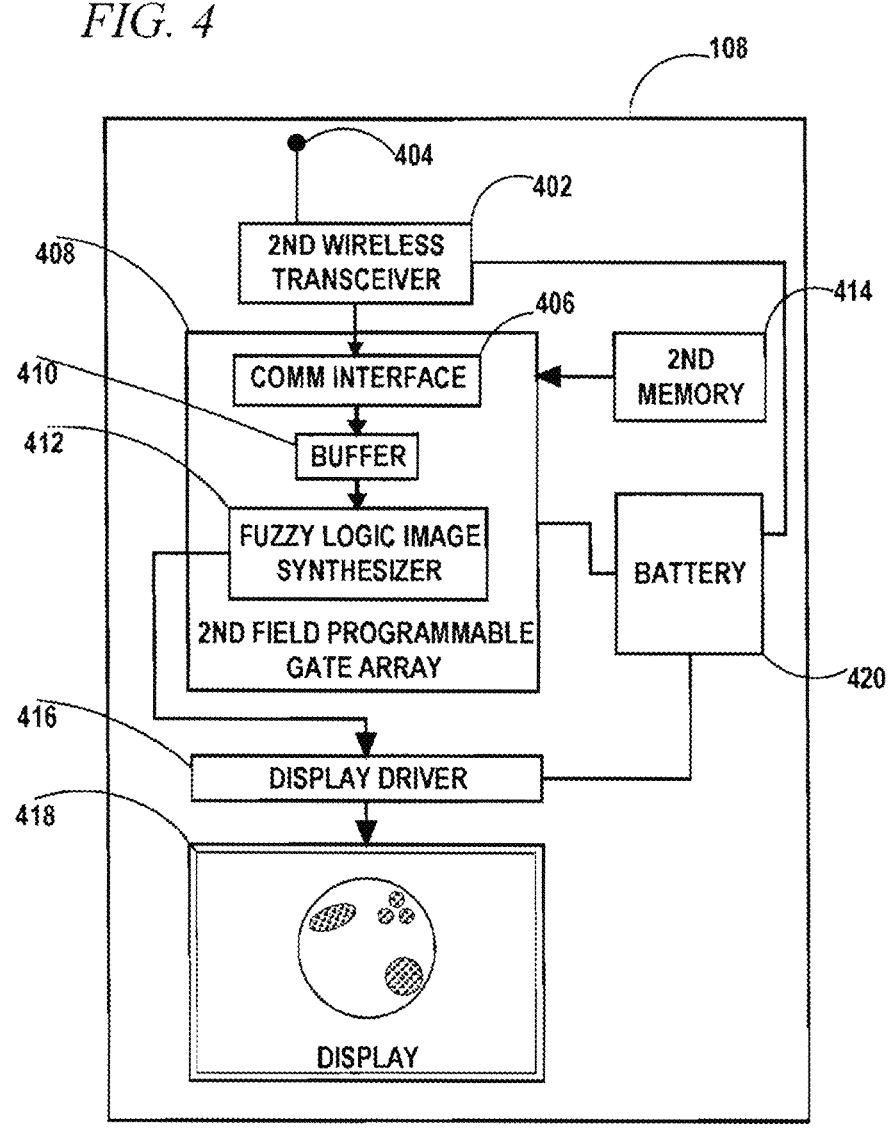
FIG. 4 is a block diagram of the handheld, wireless ECT reader shown in FIG. 1 and FIG. 3 according to one example.

FIG. 4 is a block diagram of the handheld, wireless ECT reader 108 shown in FIG. 1 and FIG. 3. The ECT reader 108 includes a second wireless transceiver 402 equipped with a second antenna 404. The second wireless transceiver 402 is selectively, wirelessly, communicatively coupled to first wireless transceiver 330 of the first ECT sensor head 102 as needed. Using the second wireless transceiver 402, the ECT reader 108 can also be selectively, wirelessly, communicatively coupled to other ECT sensor heads such as the second ECT sensor head 104 and the third ECT sensor head 106, which are also provided with wireless transceivers similar to the wireless transceiver of the first ECT sensor head 102 (not shown).

The second wireless transceiver 402 is coupled to a communication interface 406 that is implemented in a second FPGA 408. The communication interface 406 is coupled to a buffer 410 that is implemented in the second FPGA 408. The buffer 410 is used to store mutual capacitance measurements that are received from the first ECT sensor head 102 and/or other ECT sensor heads. The buffer 410 is coupled to a fuzzy logic image synthesizer 412 that is implemented in the second FPGA 408. The fuzzy logic image synthesizer 412 can alternatively be implemented as a program run on a processor, an ASIC. A processor for running a fuzzy logic image synthesizer program can be implemented in the FPGA 408 as well. A second memory 414 that stores configuration information (instructions) for the second FPGA 408 is coupled to the FPGA 408. The fuzzy logic image synthesizer 412 is coupled to a display driver 416 and the display driver 416 is coupled to a display 418. Images that are synthesized by the fuzzy logic image synthesizer 412 are output to the display driver 416 and displayed on the display 418. A light weight battery 420 powers the ECT reader 108. The battery 420 is coupled to the second field programmable gate array 408, the second wireless transceiver 402 and the display driver 416. Because the fuzzy logic image synthesizer 108 has a low computation cost, a high capacity battery which would increase the weight of the ECT reader 108 and thereby make the ECT reader 108 cumbersome to carry is not needed.

Figure 5:
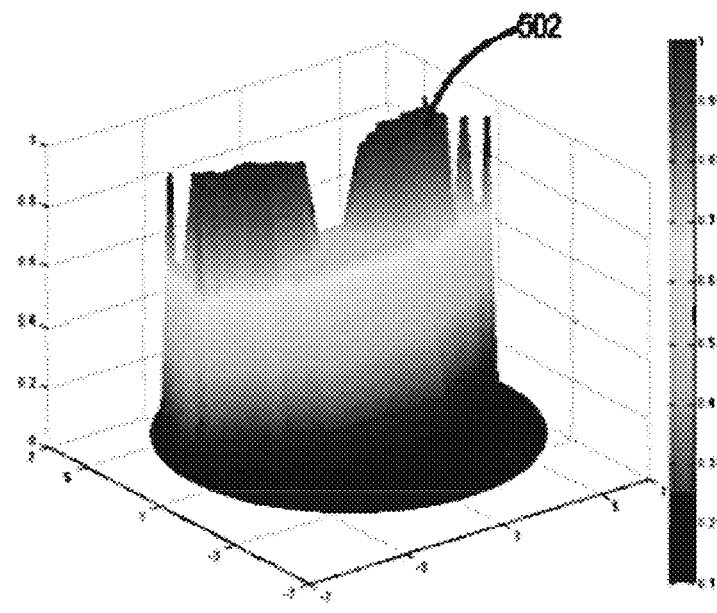
FIG. 5 is a graph including a surface plot of the sensitivity of the mutual capacitance between two particular sensing electrodes of the ECT sensor head shown in FIG. 2 to discrete changes in dielectric constant at pixel positions within a measurement domain of the ECT sensor head according to one example.

FIG. 5 is a graph 500 including a surface plot 502 of the sensitivity of the mutual capacitance between two particular sensing electrodes of the an ECT sensor head to discrete changes in dielectric constant at pixel positions within a measurement domain (region being imaged) of the ECT sensor head. FIG. 5 is for just one pair of sensing electrodes. In practice, sensitivity data will be obtained for each possible combination of electrodes (e.g., each of 66 possible combinations in the case of 12 electrodes).

The X-Y axes specify positions in the measurement domain of the ECT sensor head. Each pixel identified by a pair of indexes (i, j) where i represents a pixel row and j represents a pixel column spans a small $\Delta X$ by $\Delta Y$ region of the domain of the graph 500. The ordinate of the plot 502 indicates the sensitivity as a function of pixel position. The sensitivity of each $(i, j)^{th}$ pixel position is obtained by measuring or using electrostatic simulation to determine the mutual capacitance when the entire measurement domain with the exception of the $(i, j)^{th}$ pixel position is filled with a preselected low dielectric constant material and the $(i, j)^{th}$ pixel position is filled with a preselected high dielectric constant material. The dielectric constant of the preselected high dielectric constant material is denoted $\varepsilon_H$ and the dielectric constant of the preselected low dielectric constant material is denoted $\varepsilon_L$. The preselected low dielectric constant material and the preselected high dielectric constant material can be respectively materials having the lowest and highest dielectric constants that are expected to be present in the measurement domain of the ECT sensor head in actual use.

Figure 6:
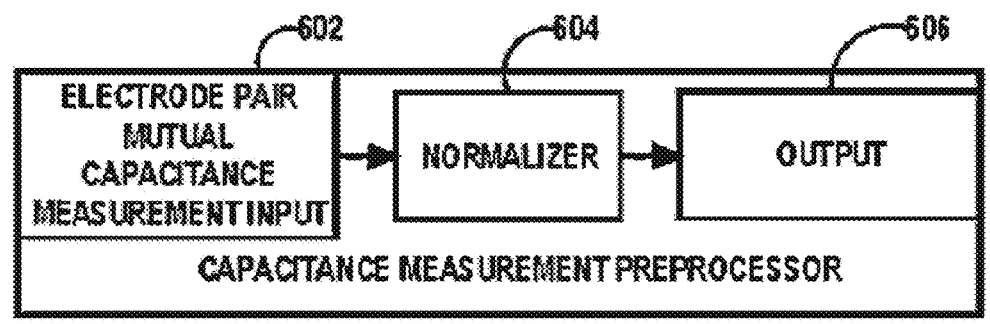
FIG. 6 is a block diagram of a capacitance measurement preprocessor according to one example.

FIG. 6 is a block diagram of a capacitance measurement preprocessor 600 of the fuzzy logic image synthesizer 412. In general, the mutual capacitance between sensing electrodes that are closer to each other will be higher. In order to compensate for this disparity, the sensitivity information of the type represented in FIG. 5 is passed through the capacitance measurement preprocessor 600. The capacitance measurement preprocessor includes an electrode pair mutual capacitance measurement input 602 coupled to a normalizer 604, which in turn is coupled to an output 606. In processing the sensitivity information represented in FIG. 5 the normalizer 604 divides the sensitivity values for each $(i, j)^{th}$ pixel by the difference between the capacitance obtained when all pixels (or the entire measurement domain) are filled with the preselected high dielectric constant material and the capacitance obtained when all pixels (or the entire measurement domain) are filled with the preselected low dielectric constant material. The operation of the capacitance measurement preprocessor on the sensitivity values can be described by equation 1 below.

$$CAP\_SENSE\_NORM(i, j, L, M) = \quad \text{EQU. 1}$$
$$\frac{(CAP((i, j) = high, L, M) - CAP\_LOW(L, M))}{(CAP\_HIGH(L, M) - CAP\_LOW(L, M))},$$

where, i indicates a pixel column,
j represents a pixel row,
L is an index identifying a first sensing electrode,
M is an index identifying a second sensing electrode, and
CAP_SENSE_NORM (i, j, L, M) is a normalized mutual capacitance measured between an $L^{th}$ sensing electrode and an $M^{th}$ sensing electrode, when the $(i, j)^{th}$ pixel is filled with the preselected high dielectric constant material and the remaining pixels are filled with the preselected low dielectric constant materials.

Further, the parameter CAP((i, j)=high, L, M) is a mutual capacitance measured between an $L^{th}$ sensing electrode and an $M^{th}$ sensing electrode, when the $(i, j)^{th}$ pixel is filled with the preselected high dielectric constant material and the remaining pixels are filled with the preselected low dielectric constant materials (plotted in FIG. 5 for one combination (L,M) of electrodes), CAP_LOW(L, M) is a mutual capacitance measured between an $L^{TH}$ sensing electrode and an $M^{TH}$ sensing electrode when all of the pixels are filled with the preselected low dielectric constant material, and CAP_HIGH(L, M) is a mutual capacitance measured between an $L^{TH}$ sensing electrode and an $M^{TH}$ sensing electrode when all of the pixels are filled with the preselected high dielectric constant material.

By implementing equation 1, the normalizer 604 will map capacitance values to the range between zero and one.

For each combination of electrodes (L, M), each $(i, j)^{th}$ pixel will be assigned to one of multiple sensitivity classes based on its sensitivity. Each unique combination of an $L^{th}$ electrode and an $M^{th}$ electrode can be identified by a single index k. The variable storing the sensitivity class is denoted sensitivity(i, j, k) where the index i denotes a pixel row, the index j denotes a pixel column and the index k denotes a combination of an sensing electrodes. For example, there may be four sensitivity classes: high, medium, low, and zero. Each $(i, j)^{th}$ pixel is assigned to a sensitivity class by determining which of several subranges of the range zero to 1, its CAP_SENSE_NORM(i, j, L, M) value it falls into. The sensitivity classes can be assigned based on rules such as follow:

If (Thresh_high<CAP_SENSE_NORM(i, j, L, M)<=1.0) then
    Sensitivity(i, j, k)="high"
If (Thresh_med<CAP_SENSE_NORM(i, j, L, M)<=Thresh_high) then Sensitivity(i, j, k)="medium"
If (Thresh_low<CAP_SENSE_NORM(i,j,L,M)<=Thresh_med) then
    Sensitivity(i, j, k)="low"
If (CAP_SENSE_NORM(i,j,L,M)<=Thresh_low) then
    Sensitivity(i, j, k)="zero"
where 0.0<Thresh_low<Thresh_med<Thresh_high<1.0.

In certain embodiments the values of the thresholds (Thresh_low, Thresh_med, Thresh_high can be coordinated with the values of the centroids of the input membership functions such as H1, H2, H3, for example, so that for the exact dielectric distribution specified for various sensitivity zones in the consequents of a set of rules for a given input that share a particular antecedent input membership (e.g., Z2), the normalized capacitance will equal the centroid of the particular input membership function. In other words, the centroids of the input membership functions may be chosen so that the converse of the fuzzy rules will be true.

The thresholds Thresh_low, Thresh_med, Thresh_high can be evenly spaced or unevenly spaced. In the latter case, different values of the thresholds can be used for different combinations of electrodes (L,M) depending on their degree of separation. For instance, if the pixels in each sensitivity class are reset to a numerical value associated with the sensitivity class, e.g., the lower bound (0, Thresh_low, Thresh_med, Thresh_high) that defines the sensitivity class, one obtains a quantized sensitivity map. The quantized sensitivity could be plotted as a surface plot (although not smooth), but can alternatively be presented as a grayscale coded heat map. FIGS. 7A-7F are grayscale coded heat map plots of quantized sensitivity within the measurement domain of the ECT sensor head 102 shown in FIGS. 1-3. As shown in FIGS. 7A-7F the measurement domain is divided into 2-D array of pixels that is cropped to conform to the circular shape of the second heterogeneous material conduit 118.

Figure 7A:
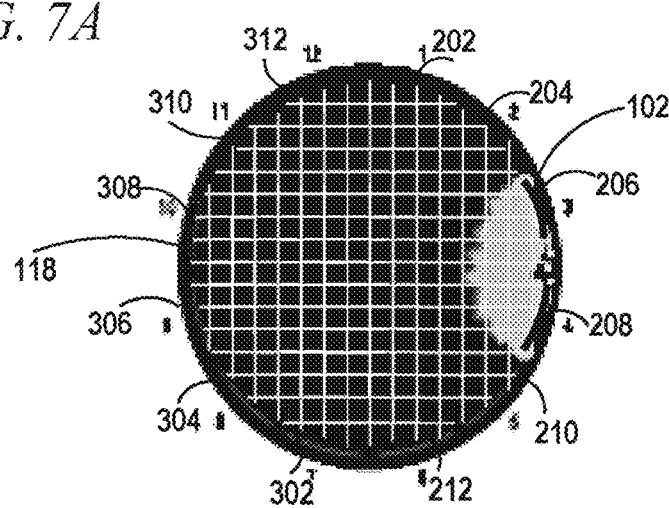
FIG. 7A is a grayscale coded heat map plots of quantized sensitivity within the measurement domain of the ECT sensor head shown in FIGS. 2-3 according to one example.
Figure 7B:
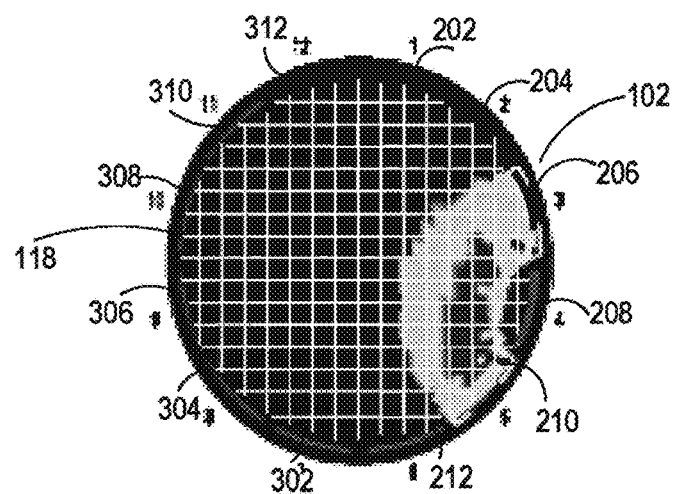
FIG. 7B is a grayscale coded heat map plots of quantized sensitivity within the measurement domain of the ECT sensor head shown in FIGS. 2-3 according to one example.
Figure 7C:
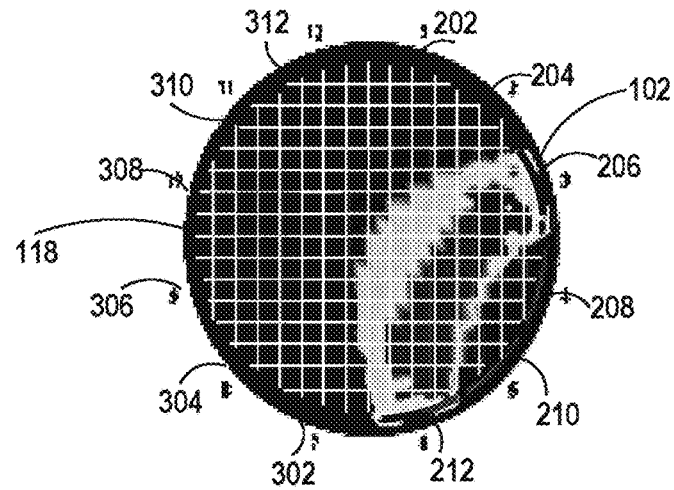
FIG. 7C is a grayscale coded heat map plots of quantized sensitivity within the measurement domain of the ECT sensor head shown in FIGS. 2-3 according to one example.
Figure 7D:
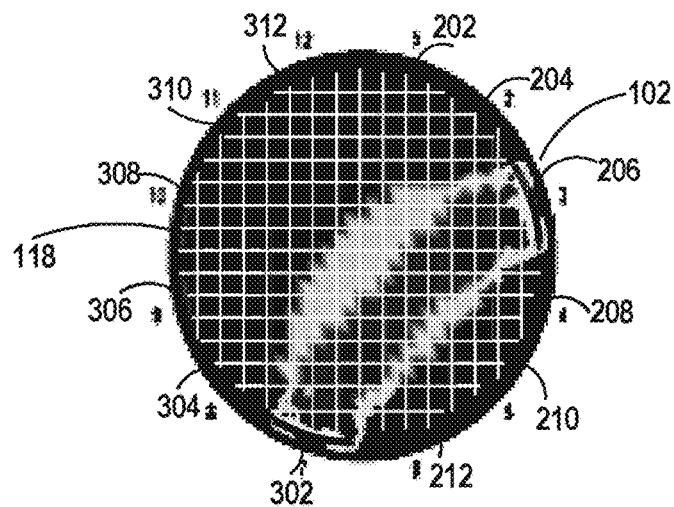
FIG. 7D is a grayscale coded heat map plots of quantized sensitivity within the measurement domain of the ECT sensor head shown in FIGS. 2-3 according to one example.
Figure 7E:
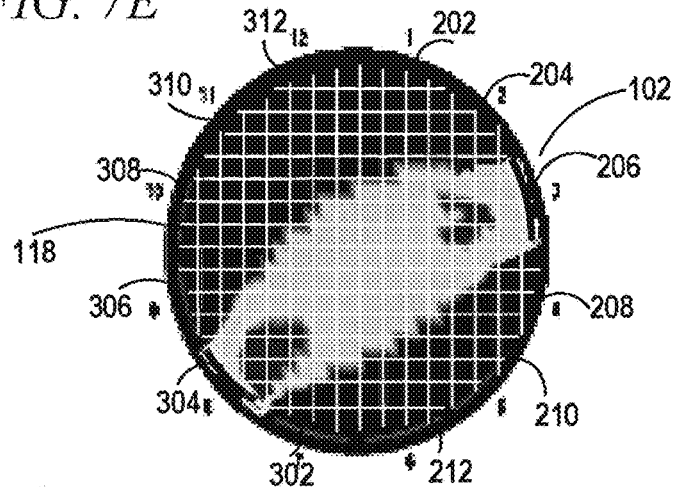
FIG. 7E is a grayscale coded heat map plots of quantized sensitivity within the measurement domain of the ECT sensor head shown in FIGS. 2-3 according to one example.
Figure 7F:
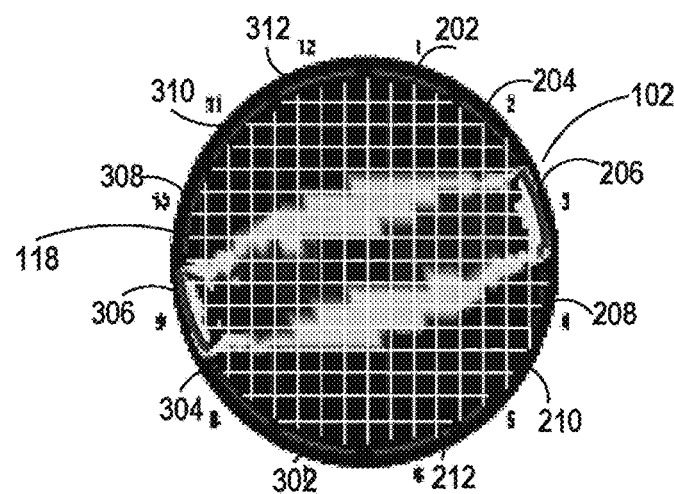
FIG. 7F is a grayscale coded heat map plots of quantized sensitivity within the measurement domain of the ECT sensor head shown in FIGS. 2-3 according to one example.

In FIGS. 7A-7F high sensitivity pixels are darkest, medium sensitivity pixels have medium darkness, low sensitivity pixels are light colored and zero sensitivity pixels are white. In each of FIGS. 7A-7F, the particular pair of sensing electrodes (L,M) which yields the quantized sensitivity map shown are identified by being drawn with a thicker line weight. Thus, FIG. 7A shows the quantized sensitivity map for the third sensing electrode 206 and the fourth sensing electrode 208 is shown. FIGS. 7A-7F represent all the possible degrees of separation for the circular 12 electrodes ECT sensor head 102. The sensitivity maps for each of the other pairs of sensing electrodes 208 is similar to one of those shown in FIGS. 7A-7F.

In addition to the sensitivity class, there is another class that depends on the degree of separation of the electrodes. To the extent that the mutual capacitance between a pair of sensing electrodes (L,M) is considered a $K^{th}$ input for the fuzzy logic image synthesizer 412, the class that depends on the degree of separation is termed the "input class". The rules concerning the degree of separation for assigning an input class will vary depending on the total number of sensing electrodes in a particular ECT sensor head. According to one example, for the 12 sensing electrode ECT sensor head 102, inputs can be assigned to input classes based on the degree of separation of the associated electrodes (L,M) as follows:

input class=1 for cases of separation by 4 or 5 electrodes;
input class=2 for cases of separation by 2 or 3 electrodes;
input class=3 for cases of separation by 1 electrode; and
input class=4 for case of directly adjacent electrodes.

Within the fuzzy logic image synthesizer 412 different fuzzy rules will be invoked depending on both the sensitivity class and the input class. Moreover, for certain input classes corresponding to widely separated sensing electrodes there will only be fuzzy rules for a certain subset of the higher sensitivity classes. For example, according to certain embodiments, for input class 1 there are only fuzzy rules that apply to the high sensitivity class. This is justified because the mutual capacitance between widely separated electrodes is low and the effect of a high dielectric being placed in a single pixel outside the high sensitivity class pixels is weak. In effect input classes for widely separated electrodes have a diminished capacity "see" the dielectric constant of material placed in lower sensitivity class pixels. Note that the area in square meters (in a 2-D cross section) in which the electric field is above a certain fraction of its maximum value is larger for widely separated electrodes while the pixel size is constant. Therefore, widely separated electrodes have a lower pre-normalization sensitivity to changes in the dielectric constant at any one pixel.

Based on the sensitivity maps it will be observed that a high dielectric constant at any one of a number of different pixel locations can give rise to a higher mutual capacitance reading. Therefore, a single mutual capacitance reading is weak evidence as to the dielectric constant of any particular pixel. However, with regard to the sensitivity maps shown in FIGS. 7A-7F it can be deduced that any given pixel will have a non-zero sensitivity class for multiple inputs (pairs of sensing electrodes). The fuzzy image synthesizer combines the weak evidence from multiple inputs to estimate the dielectric constant at each pixel location. Accumulating evidence from multiple inputs narrows down the location of high dielectric constant pixels and low dielectric pixels despite the ambiguity inherent in the fact that the sensitivity zones for each input span many pixels.

Figure 8:
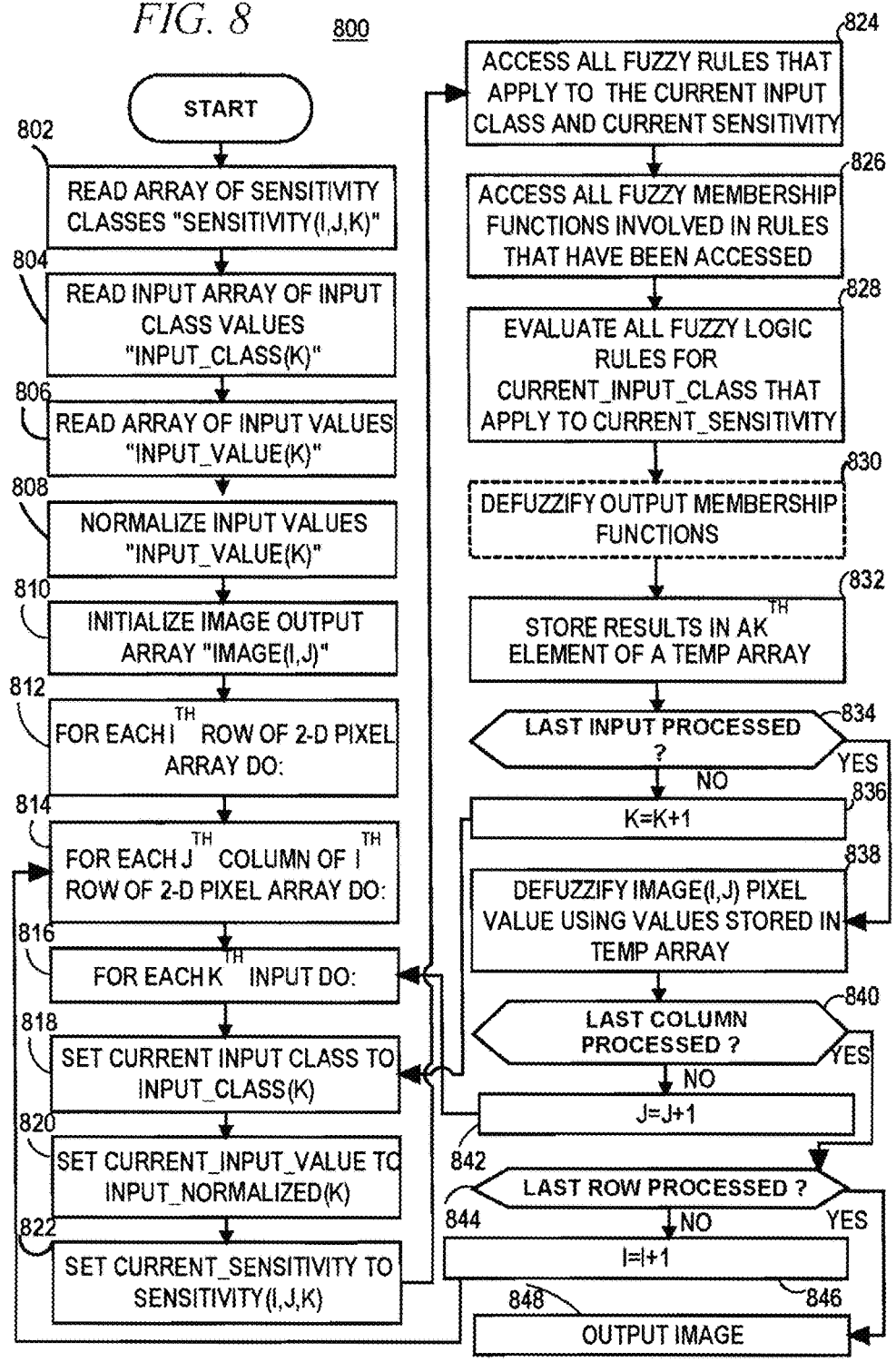
FIG. 8 is a flowchart of a fuzzy logic ECT dielectric imaging process performed in the ECT reader shown in FIG. 4 according to one example.

FIG. 8 is a flowchart of a fuzzy logic ECT imaging process 800 performed in the ECT reader 108 shown in FIG. 4. In block 802 an array that stores the sensitivity class values for each pixel for each input (pair of electrodes), is read. The stored sensitivity class values could be strings given above, i.e., "zero", "low", "medium", and "high" or integer values used in their place, e.g., 0, 1, 2, 3. The sensitivity class values can be stored in a three dimensional array, and each particular sensitivity class value can be identified as Sensitivity(i, j, k), where array index i gives a pixel row, array index j gives a pixel column, and array index k identifies an input (corresponding to a certain pair of electrodes). In the case of the ECT sensor head 102 which has 12 sensing electrodes, as discussed, there a 66 unique combinations of the 12 sensing electrodes taken two at a time with order being unimportant, so in the case of ECT sensor head 102, k takes on integer values from 1 to 66.

In block 804 an array of input class values is read. For the case of the ECT sensor head 102 the array has 66 elements. Each element of the array can be denoted Input_Class(k).

In block 806 an array of input values is read. Each element of the array can be denoted Input_Value(k). Each input value is a mutual capacitance measurement between a pair of sensing electrodes.

In block 808 the input values are normalized. According to certain embodiments the input values are normalized using equation 2 given below.

$$\text{Input\_Normalized}(k) = \frac{(\text{Input\_Value}(k) - \text{CAP\_LOW}(L, M))}{(\text{CAP\_HIGH}(L, M) - \text{CAP\_LOW}(L, M))} \quad \text{EQU. 2}$$

where, L is an index identifying a first sensing electrode;
M is an index identifying a second sensing electrode;
k is an integer index that corresponds to a particular combination of L and M values;
Input_Normalized(k) is a normalized mutual capacitance measured between an $L^{TH}$ sensing electrode and an $M^{TH}$ sensing electrode
CAP_LOW(L, M) is a mutual capacitance measured between an $L^{TH}$ sensing electrode and an $M^{TH}$ sensing electrode when all of the pixels are filled with the preselected low dielectric constant material discussed above;
CAP_HIGH(L, M) is a mutual capacitance measured between an $L^{TH}$ sensing electrode and an $M^{TH}$ sensing electrode when all of the pixels are filled with the preselected high dielectric constant material discussed above.

In block 810 an image output array is initialized. Each element of the image output array is denoted Image(i, j), where the index i is a pixel row and the index j is a pixel column.

Block 812 is the top of a first program loop that processes successive $i^{TH}$ rows of an image being produced. Next block 814 is the top of a second program loop (nested within the first program loop commenced in block 812) that processes successive pixels (in successive $J^{TH}$ columns) in each $i^{TH}$ row of the image being produced. Next block 816 is the top of a third (inner) program loop (nested with the second program loop commenced in block 814) that processes successive $k^{TH}$ inputs (normalized capacitance readings from pairs of sensing electrodes) for an $(i, j)^{TH}$ pixel.

Block 818 is the first block within the inner program loop started in block 816. In block 818 a current input class value is set to Input_Class(k)—the input class for the $k^{TH}$ pair of sensing electrodes.

In block 820 a current input value is set to the $k^{TH}$ normalized input value Input_Normalized(k).

In block 822 a current sensitivity value is set to Sensitivity (i,j,k) which is the mutual capacitance sensitivity for measurements between the $k^{TH}$ pair of electrodes with respect to changes in the dielectric constant at the $(i, j)^{TH}$ pixel.

Figure 9:
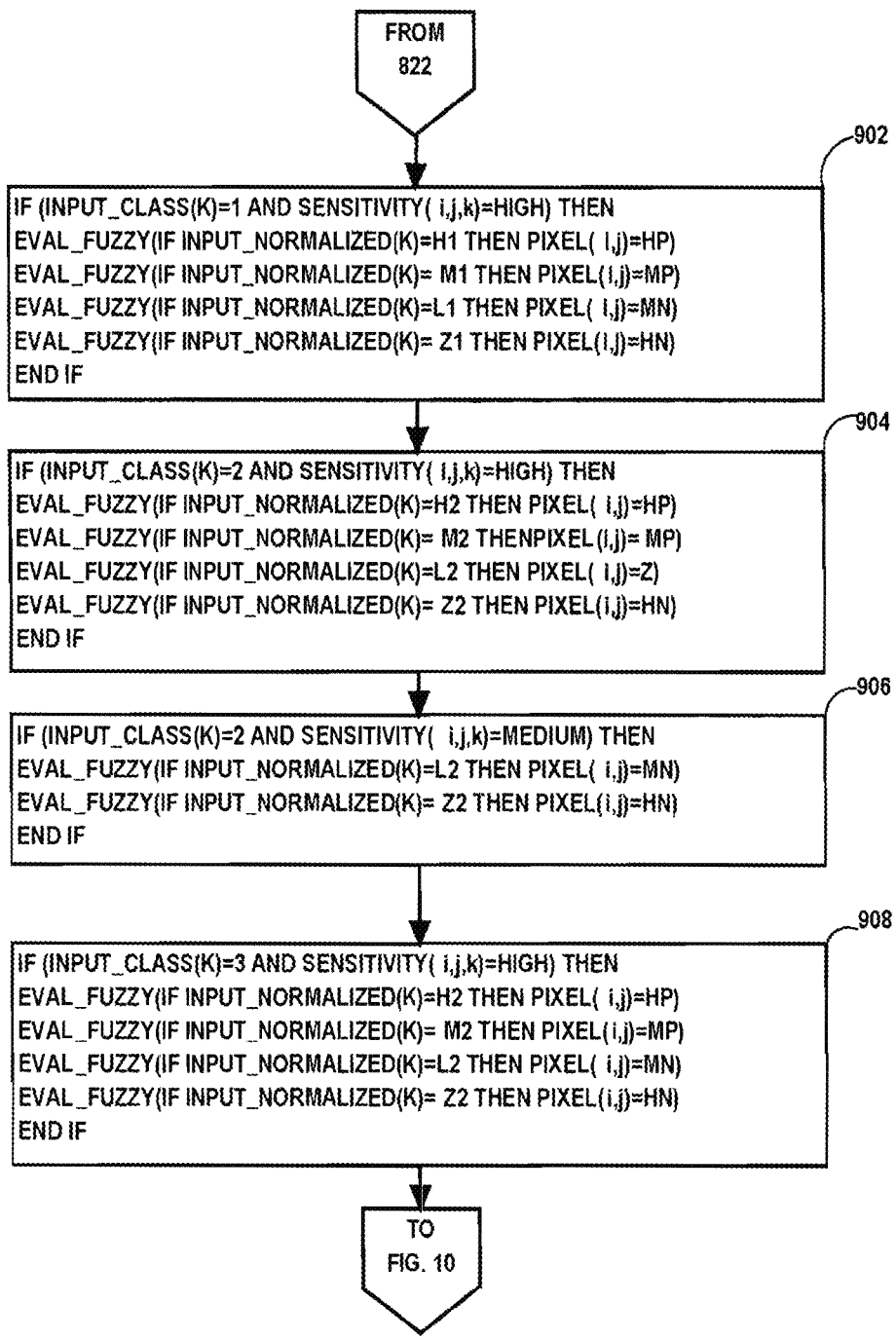
FIG. 9 is a first portion of an excerpt of a flowchart that shows certain steps of the fuzzy logic ECT dielectric imaging process shown in FIG. 5 according to one example.
Figure 10:
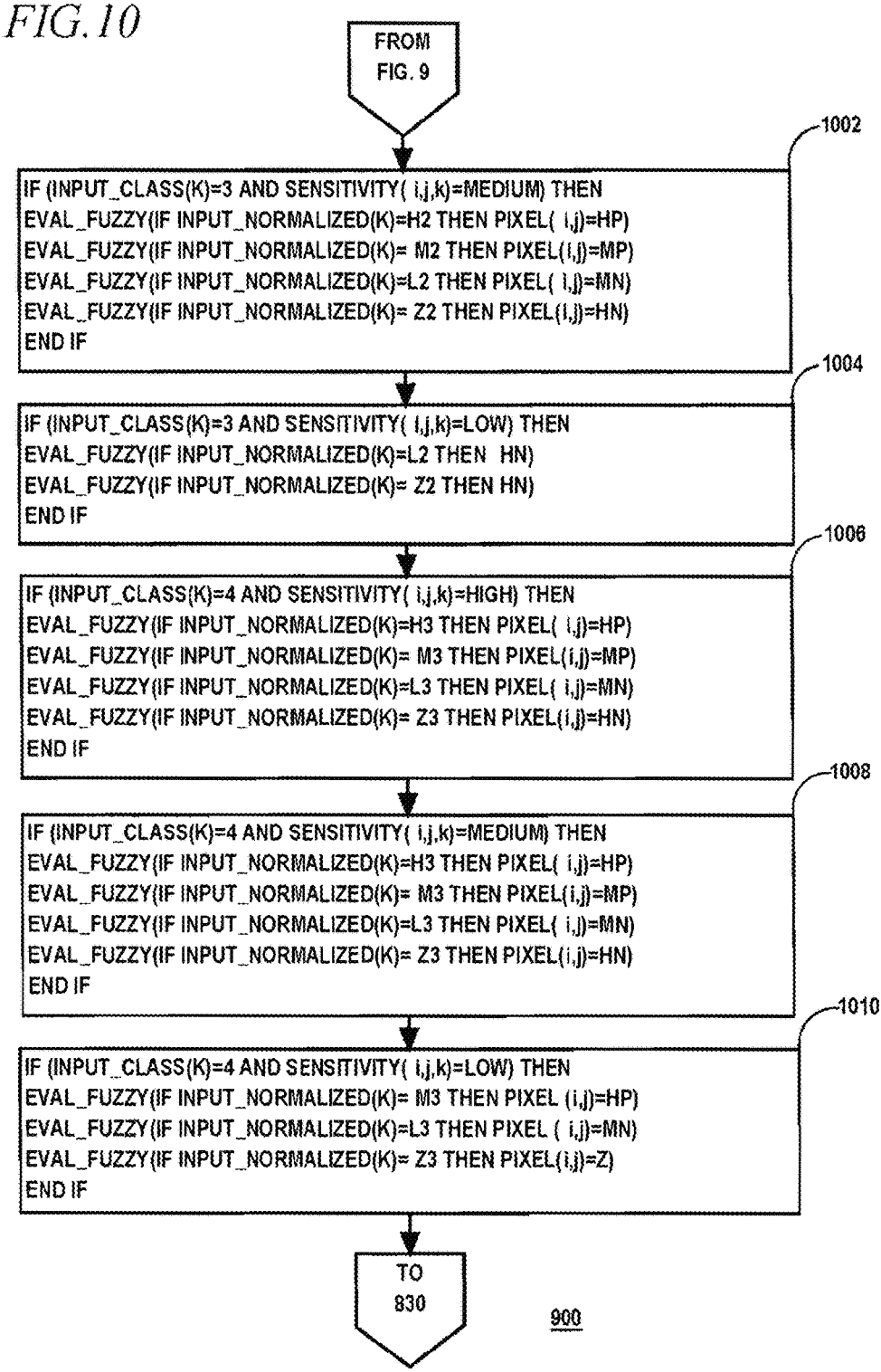
FIG. 10 a second portion of the excerpt of a flowchart commenced in FIG. 9.

In block 824 all the fuzzy rules that apply to the current input class—Input_Class(k) and the current sensitivity class Sensitivity(i,j,k) are accessed. In block 826 all fuzzy membership functions that are involved in the rules that have been accessed are accessed. (Note that the fuzzy membership functions can be included in the fuzzy rules accessed in block 826 in which case there would be no separate step 824). In block 828 all the fuzzy logic rules that apply to the current input class—Input_Class(k) and the current sensitivity value Sensitivity(i,j,k) are evaluated. Each of the fuzzy rules includes a consequent (output). FIGS. 9-10 described herein below show an implementation of blocks 822, 824 and 826 in more detail. Referring again to FIG. 8, in optional block 830 one or more output fuzzy membership functions that are included in the consequents of the fuzzy logic rules that were evaluated in block 828 are defuzzified. The result of block 830 may be a weighed centroid of the activated output membership functions in the consequents of the fuzzy rules evaluated in block 828. In block 832 the result of block 828 or 830 is stored as the $k^{TH}$ element of a temporary storage array, denoted here as TEMP(k). In the case that block 830 is not implemented information specifying output membership functions and the degree of activation can be stored in block 832. In the case that block 830 is implemented a centroid and an associated weight can be stored in block 832. Next, decision block 834 tests if the last input has been processed. When the outcome of decision block 834 is negative the process 800 proceeds to block 836 in which the index k which references successive inputs is incremented and thereafter the process 800 loops back to block 816 and continues executing as previously described. When the outcome of decision block 834 is positive meaning that the last input has been processed, then the process 800 branches to block 836 in which the $(i, j)^{TH}$ pixel is defuzzified using all the information (either activated output membership functions or weighted centroids) stored in the temporary storage array in which values were stored in block 832.

Next decision block 840 tests if a last column of the current $i^{TH}$ row of the image has been processed. If the outcome of decision block 840 is negative meaning that the more pixels in the $i^{TH}$ row remain to be processed, then the process 800 proceeds to block 842 in which the index j that points to successive pixels within the each $i^{TH}$ row is incremented and thereafter the process 800 loops back to block 816 and continues executing as previously described. If on the other hand, the outcome of decision block 840 is positive meaning that all of the pixels in the $i^{TH}$ row have been processed, then the process 800 branches to decision block 844 the outcome of which depends on whether the last row has been processed. If the outcome of decision block 844 is negative meaning that more rows remain to be processed, then the process 800 proceeds to block 846 in which the index i which points to successive rows is incremented and thereafter the process 800 loops back to block 814 and continues executing as previously described. If on the other hand the outcome of decision block 844 is positive meaning that all of the rows of the image have been generated then process proceeds to block 848 and outputs an image including all of the pixels on display 418.

Figure 11:
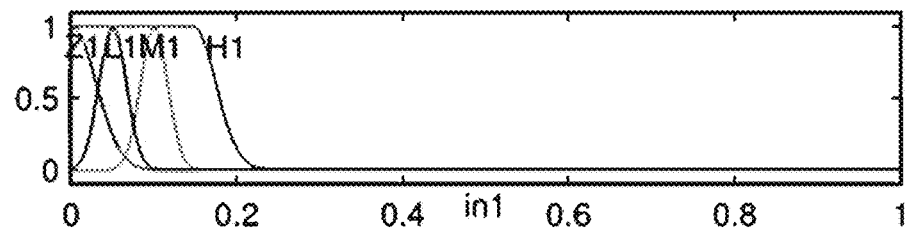
FIG. 11 is a plot of an input fuzzy membership function that is used in the fuzzy rules that are evaluated in the steps shown in FIGS. 9-10 according to one example.
Figure 12:
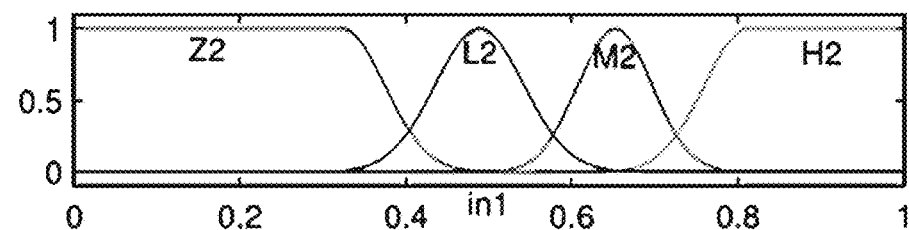
FIG. 12 is a plot of an input fuzzy membership function that is used in the fuzzy rules that are evaluated in the steps shown in FIGS. 9-10 according to one example.
Figure 13:
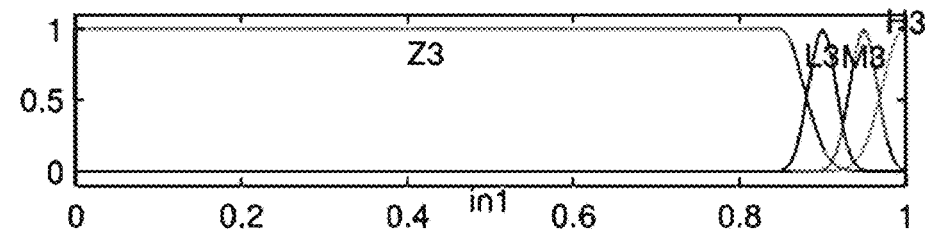
FIG. 13 is a plot of an input fuzzy membership function that is used in the fuzzy rules that are evaluated in the steps shown in FIGS. 9-10 according to one example.

FIGS. 9-10 show an excerpt of a flowchart of a subprocess 900 that that is more detailed than blocks 822, 824, 826. The process 900 shown in FIGS. 9-10 is used to perform the functions of blocks 822, 824, 826 according to one example. Each of the blocks 902, 904, 906, 908, 910, 1002, 1004, 1006, 1008, 1010 of the process 900 includes multiple fuzzy logic rules within a Boolean conditional statement for executing the fuzzy logic rules. The Boolean conditional statement in each block specifies an input class which is stored in the array Input_Class and a sensitivity class which is stored in the array Sensitivity. On each pass through the blocks 902, 904, 906, 908, 910, 1002, 1004, 1006, 1008, 1010 the Boolean conditional statement in only one of the blocks will be met because the Boolean conditional statements within the blocks 902, 904, 906, 908, 910, 1002, 1004, 1006, 1008, 1010 are mutually exclusive. Each block addresses a different combination of input class and sensitivity class. In FIGS. 9-10 the token "EVAL_FUZZY" means that the expression in the following parenthesis is an fuzzy logic IF..THEN statement. Each fuzzy logic IF..THEN statement has an antecedent and a consequent. For example referring to the first fuzzy rule in block 902 the antecedent is Input_Normalized(k)=H1 and the consequent is PIXEL(i, j)=HP. The antecedent evaluates to a degree of fuzzy membership that the Input_Normalized(k) value has in an input membership function H1. FIGS. 11-13 are plots of input fuzzy membership functions that are used in the fuzzy rules that are evaluated in the steps shown in FIGS. 9-10. FIG. 11 in particular includes a plot of input membership function H1 along with other input membership functions Z1, L1, M1 that are part of other fuzzy rules that are used in block 902. Because the input membership functions Z1, L1, M1, and H1 are overlapping a particular value of the Input_Normalized(k) will typically have finite degrees of membership in multiple input membership functions. Note also that the input membership functions Z1, L1, M1, H1 shown in FIG. 11 are used in the case that the Input_Class(k)=1. Because Input class 1 corresponds to widely separated sensing electrodes, with the electric field spanning between the sensing electrodes spread over a volume that is large compared to the size of one pixel, placing a high dielectric constant at any one specific pixel will a relatively low effect on increasing mutual capacitance between the sensing electrodes hence all of the input fuzzy membership functions Z1, L1, M1, H1 are shifted to positions near zero.

Blocks 904 and 906 include fuzzy rules applicable if the Input_Class(k)=2. Block 904 is applicable if Sensitivity(i,j, k) is high and block 906 is applicable if the Sensitivity(i,j,k) is medium. Blocks 908, 1002, and 1004 include fuzzy rules applicable if the Input_Class=3. Block 908 is applicable if the Sensitivity(i,j,k) is high, block 1002 is applicable if the Sensitivity(i,j,k) is medium and block 1004 is applicable is the Sensitivity(i,j,k) is low. The antecedents of the fuzzy rules used in blocks 904, 906, 908, 1002, 1004 involve fuzzy membership functions H2, M2, L2, and Z2 shown in FIG. 12. The fuzzy membership functions H2, M2, L2, and Z2 are more evenly distributed over the range zero to one. Blocks 1006, 1008, 1010 include fuzzy rules applicable if the Input_Class=4. Block 1006 is applicable if the Sensitivity (i,j,k) is high, block 1008 is applicable if the Sensitivity(i, j,k) is medium and block 1010 is applicable if the Sensitivity (i,j,k) is low. The antecedents of the fuzzy rules used in blocks 1006, 1008, 1010 involve fuzzy membership functions H3, M3, L3, and Z3 shown in FIG. 13. The consequents of all of the fuzzy rules in FIGS. 9-10 use output membership functions HN, MN, Z, MP, HP shown in FIG. 14. The input membership functions shown in FIGS. 11-13 are either Gaussian as in the cases of Z1, L1, M1, L2, M2, L3, M3 and H3 or piecewise defined functions that are one-half of a Gaussian function connected at its peak to a constant value line as in the cases of H1, Z2, H2 and Z3. According to alternative embodiments other shapes of fuzzy membership functions are used. For example the fuzzy membership functions can be trapezoidal functions defined by four points, or triangles defined by three points.

FIGS. 15-18 illustrate in graphical form the evaluation of the fuzzy logic IF..THEN rules (e.g., IF INPUT_NORMALIZED(K)=H1 THEN PIXEL(i, j)=HP) that are used in the process 900 shown in FIGS. 9-10.

Figure 14:
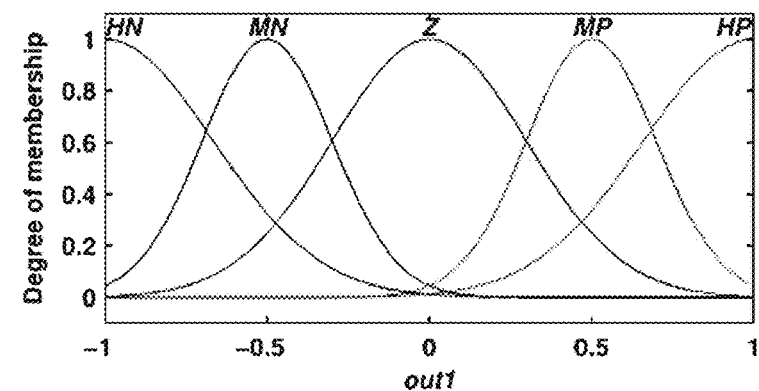
FIG. 14 is a plot of output fuzzy membership functions that are used in the rules that are evaluated in the process shown in FIGS. 9-10 according to one example.
Figure 15:
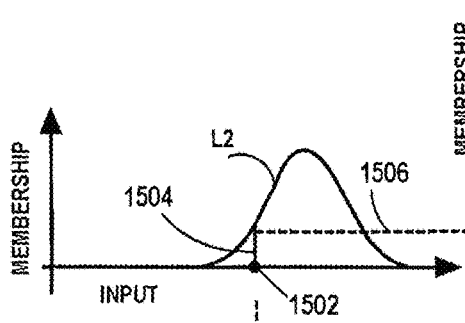
FIG. 15 shows the activation of an input fuzzy membership function of the type which appears in the antecedent of certain fuzzy rules of the type used in steps shown in FIGS. 9-10 according to one example.
Figure 16:
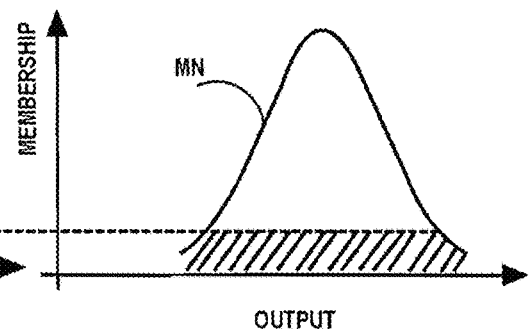
FIG. 16 shows the activation of an output fuzzy membership function in a fuzzy rule consequent in response to the activation of the input fuzzy membership function shown in FIG. 15 according to one example.

FIG. 15 includes a plot of the L2 input fuzzy membership function that is also included in FIG. 12 along with other input fuzzy membership functions. The input fuzzy membership function L2 appears in the antecedent of certain fuzzy rules of the type used in steps shown in FIGS. 9-10. FIG. 16 is a plot of the output membership function MN that is also plotted in FIG. 14. The output fuzzy membership function MN appears in the consequent of certain fuzzy rules in certain steps shown in FIGS. 9-10 and in certain cases is activated in response to the activation of the input fuzzy membership function L2 shown in FIG. 15.

Figure 17:
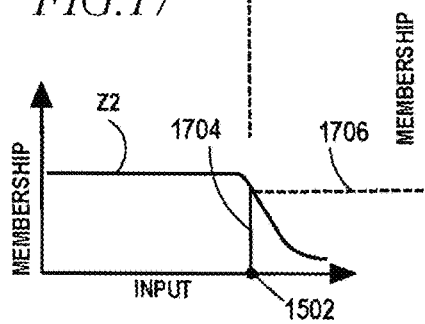
FIG. 17 shows the activation of another input fuzzy membership function of the type which appears in the antecedent of certain fuzzy rules of the type used in steps shown in FIGS. 9-10 according to one example.

In FIG. 15 as well as in FIG. 17 the abscissa corresponds to an input value, which in the case of the fuzzy logic image synthesizer 412 is a value of the Input_Normalized(k) capacitance variable discussed above. In FIG. 15 an exemplary input value is marked by a dot 1502. A vertical line 1504 extends from the dot 1502 to the input membership function L2 and a horizontal line 1506 extends from the point of intersection of the vertical line 1504 and the input membership function L2 across the output membership function MN in FIG. 16. According to this embodiment the output membership function MN is clipped at the level of the horizontal line. According to alternative embodiments output put membership functions such as MN can be scaled so that their peak is at the level of the horizontal line 1506.

Figure 18:
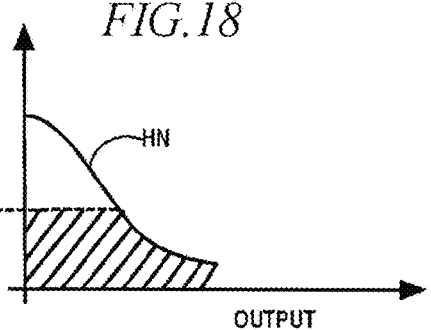
FIG. 18 shows the activation of another output fuzzy membership function in a fuzzy rule consequent in response to the activation of the input fuzzy membership function shown in FIG. 17 according to one example.

FIG. 17 shows the activation of another input fuzzy membership function Z2 of the type which appears in the antecedent of certain fuzzy rules of the type used in steps shown in FIGS. 9-10. FIG. 17 includes a plot of the Z2 input membership function that is also included in FIG. 12 along with the L2 input membership function. FIG. 17 shows the activation of the input membership function Z2 at the same value of Input_Normalized(k) identified by dot 1502 that is shown in FIG. 15. Note, that both input fuzzy membership functions L2 and Z2 appear in blocks 904, 906, 908, 1002, 1004 of process 900. When anyone of the latter blocks is executed and the value of both L2 and Z2 is non-zero at the Input_Normalized(k) value, both fuzzy input membership functions L2 and Z2 will be activated to a finite degree and output fuzzy membership functions in associated consequents will be activated to a finite degree. Analogously, other combinations of fuzzy input membership functions that appear together in the same block of process 900 and overlap (as shown in FIGS. 11-13) can be concurrently activated depending on the value of Input_Normalized(k). FIG. 18 shows the activation of another output fuzzy membership function HN in a fuzzy rule consequent (e.g., in the second fuzzy rule in block 1004) in response to the activation of the input fuzzy membership function Z2 shown in FIG. 17. Referring again to FIG. 17 a second vertical line 1704 extend from the dot 1502 on the abscissa of FIG. 17 which marks the value of Input_Normalized(k) to the fuzzy input membership function Z2, and a second horizontal line 1706 extends from the intersection of the second vertical line 1704 and the fuzzy input membership function Z2 across the output fuzzy membership function HN in FIG. 18. As shown in FIG. 18 the output fuzzy membership function HN is clipped at the level of the second horizontal line 1706. However as in the case of the output membership function MN discussed above and in the case of other output fuzzy membership functions, alternatively the output fuzzy membership function HN can be scaled so that its peak is at the level of the second horizontal line 1706 instead of being clipped.

As shown in FIG. 14 the domain over which the output membership functions are defined extends from −1 to +1. The domain of the output membership functions relate to the dielectric constant of regions, e.g., pixels of the measurement domain of the ECT sensor system 300. Per equation 3 below dielectric constants of materials in the measurement domain of the ECT sensor heads are normalized to the range zero to +1.

$$\varepsilon_N = \frac{\varepsilon - \varepsilon_L}{\varepsilon_H - \varepsilon_L} \qquad \text{EQU. 3}$$

where $\varepsilon_N$ is a normalized dielectric constant;

$\varepsilon$ is an actual dielectric constant;

$\varepsilon_H$ is the high preselected dielectric constant discussed above which corresponds to the highest dielectric constant material expected to be present in the measurement domain of a particular ECT sensor head; and $\varepsilon_L$ is the low preselected dielectric constant discussed above which corresponds to the lowest dielectric constant material expected to be present in the measurement domain of a particular ECT sensor head.

In response to certain normalized capacitance readings (between certain pairs of sensing electrodes), certain of the fuzzy logic rules in process 900 will activate output membership functions that have positive valued centroids which correspond to high dielectric constants. In response to other normalized capacitance readings (between other pairs of sensing electrodes) certain fuzzy logic rules in process 900 will activate output membership functions that have negative valued centroids. The final defuzzified result for a given pixel can be based on activation output membership functions having both positive valued and negative valued centroids, which in the process of defuzzification will be combined. A defuzzified dielectric constant that is negative will be set to zero.

Each of the blocks of process 900 includes multiple fuzzy logic rules that include multiple fuzzy input membership functions two or more of which can have non-zero values at a given value of input, leading to non-zero activation of multiple fuzzy output membership functions. All of the activated membership functions that apply to each $(i, j)^{th}$ pixel, each of which is obtained from a different execution of the process 900 within the loop started in block 816, can be defuzzified in one step, e.g., in block 830 shown in FIG. 8. Alternatively, the final output of the block of process 900 that is executed in a given execution of process 900, may be reduced to a single weighed centroid value with a weight equal to the area of the activated (e.g., clipped) output membership functions. All such weighted centroid values that are obtained from a subset of inputs that have non-zero sensitivity values for a given $(i, j)^{th}$ pixel can be combined to obtain a final centroid for the $(i, j)^{th}$ pixel in a final defuzzification stage.

Figure 19:
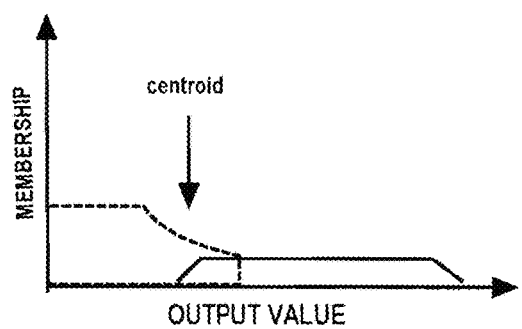
FIG. 19 shows the activated output membership functions shown in FIG. 16 and FIG. 18 which are used to obtain a defuzzified (crisp) output value according to one example.

FIG. 19 illustrates a process of defuzzification according to one example. FIG. 19 shows the result of applying the calculating a centroid of two activated (clipped) output fuzzy membership functions MN and HN shown in FIG. 16 and FIG. 18 respectively. The centroid function accepts multiple (in the illustrated example of FIG. 19 two) single independent variable functions-in particular the activated (e.g., clipped) output membership functions as input and in produces single independent variable value. The centroid is marked in FIG. 19. As stated above in each execution of process 900 the Boolean conditional statement for execution of the fuzzy rules will only be met in one of the blocks 902-908, 1002-1010 of process 900 because each block corresponds to a different combination of input class and sensitivity class. The output of the block of the process 900 for which the Boolean execution criteria is met can be information or signals specifying a set of activated (e.g., clipped) output membership functions, or a centroid weighed by the integral of the activated membership functions. Because process 900 is within the inner loop commenced in block 816 (FIG. 8) which runs through successive inputs (pairs of sensing electrodes), the aforementioned set of activated output membership functions or alternatively the aforementioned weighted centroid is each merely one contribution to a final output for a given pixel. The final pixel value will be based on many contribution derived from many inputs.

The fact that the various sensitivity zones (zero, low, medium, high) for each input (pair of sensing electrodes) span multiple pixels, which is related, in part, to the spreading of electric field lines traversing from one sensing electrode to another according to the electric field equation, introduces an ambiguity in identifying a specific pixel that includes a material having a high or low dielectric constant. The ambiguity is resolved by the fuzzy logic synthesizer 412 to a degree that reasonably accurate images can be produced by combining outputs obtained from multiple inputs (pairs of sensing electrodes). While the sensitivity zones from different inputs overlap they do so only partially and therefore the information provided by the different inputs is only partially redundant. A high mutual capacitance reading from a first input (pair of sensing electrodes) is taken (according to the fuzzy rules of process 900) as a tentative indication that all of the pixels in a first high sensitivity zone associated with the first input include a high dielectric material. However the tentative indication can be negated in respect to a subset of the pixels of the first high sensitivity zone if, for example, a second high sensitivity zone of a second input includes the subset and a low mutual capacitance reading is obtained from the second input. To the extent that each pixel will be within a number of high sensitivity zones, medium and/or low sensitivity zones, it will be appreciated that many inputs can contribute to correction of the first tentative indication from just one input.

A description of a process of heterogeneous dielectric fuzzy logic ECT imaging is presented in the form of flowcharts in FIGS. 8-10 as a way of communicating aspects of certain embodiments, however fuzzy logic ECT imaging of heterogeneous dielectric materials according to teachings herein need not be implemented using a processor (e.g., microprocessor, microcontroller) running a program. Alternatively, the same or equivalent functions of the ECT imaging of heterogeneous dielectric materials that are included in the processes 800, 900 shown in FIGS. 8-10 can be implemented in an Application Specific Integrated Circuits (ASICs) or FPGAs.

Figure 20:
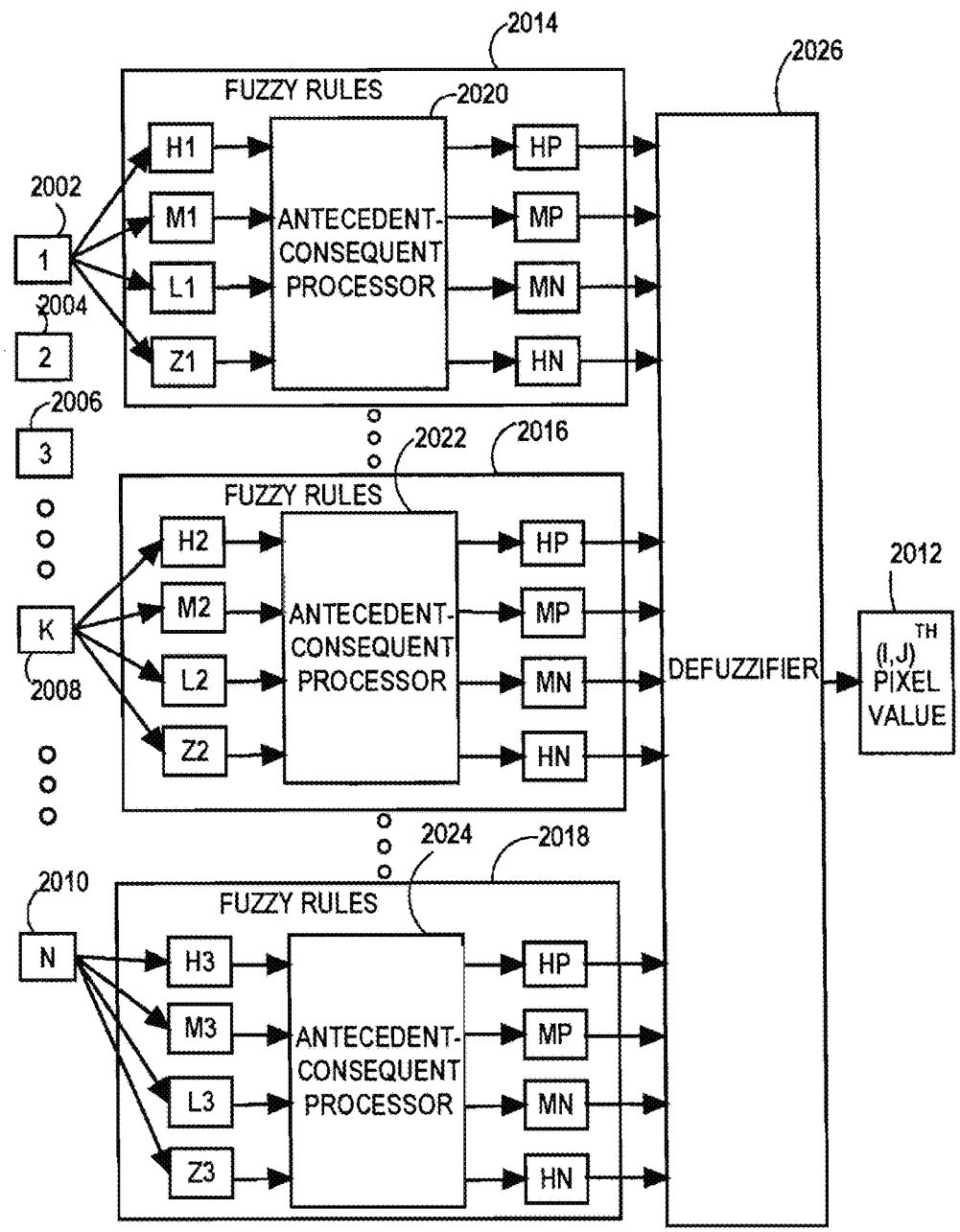
FIG. 20 shows a portion of a fuzzy logic ECT dielectric imaging synthesizer which produces one particular pixel value of an image according to one example.

FIG. 20 shows a portion of a fuzzy logic ECT heterogeneous dielectric imaging synthesizer 2000 which produces one particular pixel value of an image. It should be understood that the complete system 2000 including the portion shown in FIG. 20 has many such portions in order to produce many pixel values of a complete image. All such portions can be implemented as separate chains in an ASIC, FPGA, or multicore computer. At the left of FIG. 20 are a plurality of inputs 2002, 2004, 2006, 2008, 2010 including a first input 2002, a second input 2004, a third input 2006, a $K^{TH}$ input 2008 and an $N^{TH}$ input 2010. N is the number of inputs which can vary in different embodiments. Ellipses are present between inputs 2002, 2004, 2006, 2008, 2010 to indicate the presence of additional inputs not shown. Each of the inputs 2002, 2004, 2006, 2008, 2010 receives a normalized mutual capacitance reading (denoted "Input_Normalized" above). The value of an $(i, j)^{TH}$ pixel 2012 is shown at the right of FIG. 20. A given $(i, j)^{TH}$ pixel will be in the sensitivity zones, be they high, medium or low, of multiple pairs of sensing electrodes. For the purpose of illustration it is assumed that that the $(i, j)^{TH}$ pixel in FIG. 20 is within a high sensitivity zone associated with the first input 2002, a high sensitivity associated with the $K^{TH}$ input and a medium sensitivity zone associated with the $N^{TH}$ input. In practice a given $(i, j)^{TH}$ pixel can be within more than three sensitivity zones, however three is used here for the purpose of illustration.

The first input 2002 is coupled to four fuzzy input membership functions H1, M1, L1, Z1 (see plot representations in FIG. 11) of a first set of fuzzy rules 2014; the $K^{TH}$ input 2008 is coupled to four input membership functions H2, M2, L2, Z2 (see plot representations in FIG. 12) of a second set of fuzzy rules 2016; and the $N^{TH}$ input 2010 is coupled to four input membership functions H3, M3, L3, Z3 (see also FIG. 13) of a third set of fuzzy rules 2018. In a microprocessor, ASIC or FPGA implementation the input fuzzy membership functions H1, M1, L1, Z1, H2, M2, L2, Z2, H3, M3, L3, Z3 of the fuzzy rules 2014, 2016, 2018 can be implemented using look up tables (LUT). In reference to the first set of fuzzy rules 2014, a set of degrees of membership that are output by the input fuzzy membership functions H1, M1, L1, Z1 are processed by a first antecedent-consequent processor 2020 which activates each of the set of output membership functions HN, MN, Z, MP, HP (see also FIG. 14) to a degree that is dependent on the degree of membership of an input value received at the first input 2002. One form of antecedent-consequent relation is illustrated in FIGS. 15-16 and in FIGS. 17-18. Alternative forms of antecedent-consequent relations can also be used. The second 2016 and third 2018 sets of fuzzy rules respectively include a second antecedent-consequent processor 2022 and a third antecedent-consequent processor 2024 which function in the same manner as the first antecedent-consequent processor 2020 to activate the separate copies of the output membership functions HP, MP, MN, HN that are included in the second set of fuzzy rules 2016 and the third set of fuzzy rules 2018. The sets of output membership functions HP, MP, MN, HN of the first set of fuzzy rules 2014, the second set of fuzzy rules 2016 and the third set of fuzzy rules 2018 are in general activated to different degrees due to the difference in the values of the Normalized_Input at the first input 2002, the $K^{TH}$ input 2008 and the $N^{TH}$ input 2010 and due to the inclusion of different sets of input membership functions in each set of fuzzy rules 2014, 2016, 2018. The output membership functions having been activated to various degrees are fed into a defuzzifier 2026 which produces the $(i, j)^{TH}$ pixel value 2012.

Figure 21:
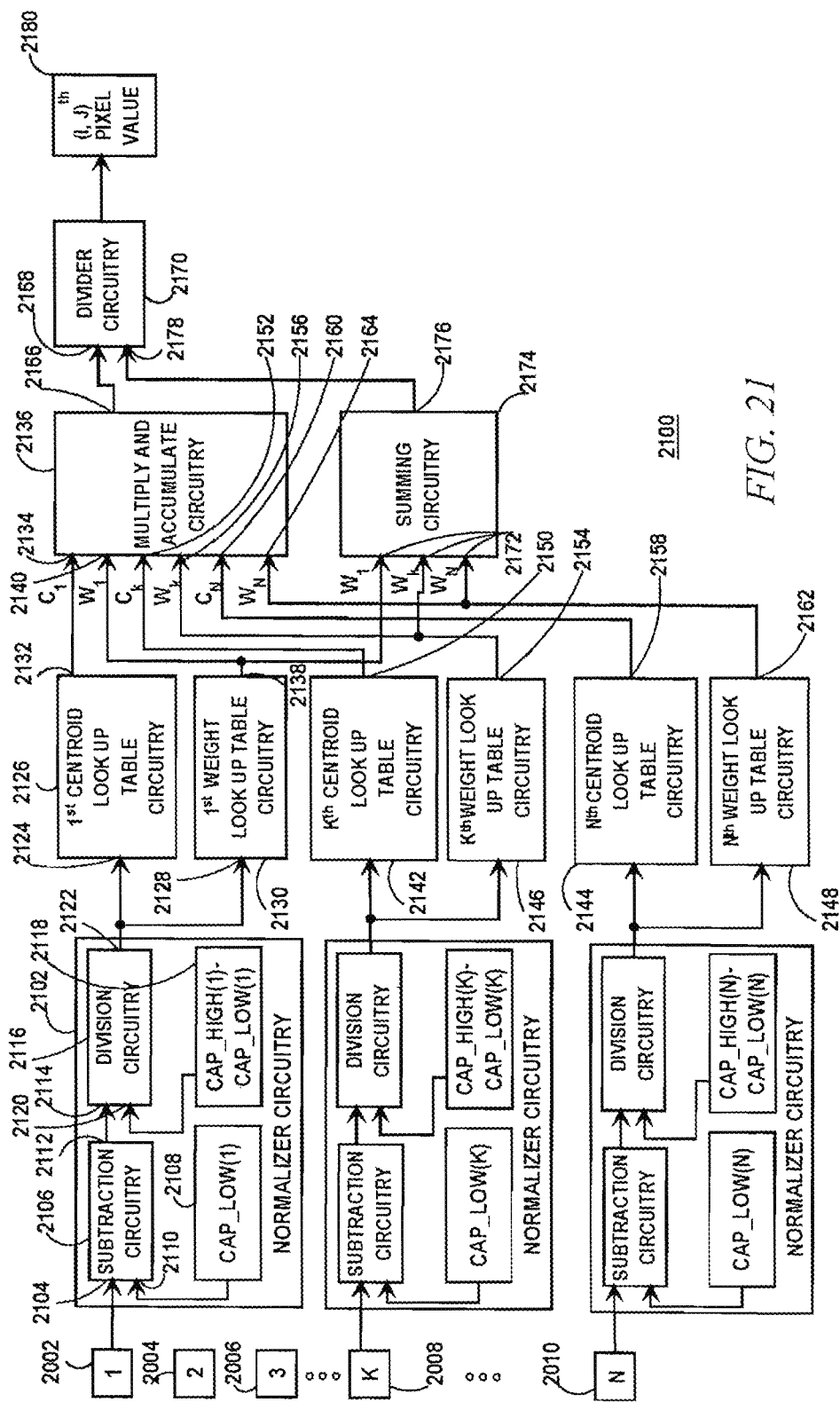
FIG. 21 shows an FPGA implementation of a portion of a fuzzy logic ECT image synthesizer which produces one particular pixel value of an image according to one example.

FIG. 21 shows an FPGA 2100 implementation of a portion of a fuzzy logic ECT heterogeneous dielectric imaging synthesizer 2000 which produces one particular $(i, j)^{th}$ pixel value 2180 of an image. The FPGA 2100 implementation shown in FIG. 21 can be incorporated into the FPGA 408 of the ECT reader 108. The inputs 2002, 2004, 2006, 2008, 2010 which receive mutual capacitance measurements from the sensing electrodes 202, 204, 206, 208, 210, 212, 302, 304, 306, 308, 310, 312 of the ECT sensor head e.g., 102 are shown at the left of FIG. 21.

In FIG. 21, processing circuitry for processing three inputs including the first input 2002, the $K^{th}$ input 2008 and the $N^{th}$ input 2010 is shown for the purpose of illustration, however in practice more than three inputs can be processed to produce each particular $(i, j)^{th}$ pixel value 2080 if the particular $(i, j)^{th}$ pixel 2080 is within non-zero sensitivity zones for more than three pairs of sensing electrodes. The processing of the mutual capacitance measurements that are received at the first input 2002 will be described in detail herein below, it being understood that the processing of the $K^{th}$ input 2008 and the processing of the $N^{th}$ input 2010 are analogous. However, for a given $(i, j)^{th}$ pixel the processing of different inputs may differ, in so far as the particular set of fuzzy rules (separate sets of fuzzy rules are shown in a separate blocks in FIGS. 9-10) which is used differ because different inputs have different input classes and the $(i, j)^{th}$ pixel may be in differing sensitivity zones for different inputs.

Entering now upon a detailed account of the processing of the signal impressed at the first input 2002, with reference to FIG. 21 it is seen that the first input 2002 is coupled to normalizer circuitry 2102 implemented in the FPGA 2100. Within the normalizer circuitry 2102 the first input 2002 is coupled to a first operand input 2104 of subtraction circuitry 2106. A CAP_LOW memory 2108 which stores the CAP_LOW(L, M) value (a constant) for the first input 2100 is coupled to a second operand input 2110 of the subtraction circuitry 2106. Note that in FIG. 21 the indexes L, M of CAP_LOW and CAP_HIGH which refer to a pair of electrodes are replaced by a single corresponding index identifying the pair of electrodes as an input.

A result output 2112 of the subtraction circuitry 2106 is coupled to a first argument input 2114 of division circuitry 2116. A CAP_HIGH-CAP_LOW memory 2118 that stores the value of CAP_HIGH minus CAP_LOW (a constant) is coupled to a second operand input 2120 of the division circuitry 2116. The operation of the normalizer is described by equation 2 given above.

A result output 2122 of the division circuitry 2116, which serves as an output of the normalizer circuitry 2102, is coupled to an address input 2124 of first centroid Look Up Table (LUT) circuitry 2126, and to an address input 2128 of first weight LUT circuitry 2130. The first centroid LUT circuitry 2126 and the first weight LUT circuitry 2130 together represent the set of rules in one of the blocks of FIG. 9 and FIG. 10. For example if the first input 2002 is based on a pair of sensing electrodes that based on their degree of separation are in input class 1 and in respect to which the $(i, j)^{th}$ pixel is in a high sensitivity class, then the first centroid LUT circuitry 2126 and the first weight LUT circuitry 2130 together implement in hardware the set of rules in block 902. Block 902 includes four fuzzy rules.

For any given normalized input value, the fuzzy rules in each of the blocks of FIG. 9 and FIG. 10 will often have non-zero membership values in more than one input membership function, leading to finite activation of more than one output membership function and such output membership functions activated to a degree that they are based on the given normalized input will have a centroid and an integral. The integral is used as a weight. Centroids of the sum of two or more functions can be computed directly or in stages by computing a weighted sum of centroids of mutually exclusive subsets of three or more functions. For example, the centroid of each individual function can be computed and then a weighted sum of the individual centroids can be computed where the weight for each centroid is the integral of the corresponding function. The first centroid LUT circuitry 2126 captures the functional relationship between the value of the Input_Normalized signal output by the division circuitry 2116 and the value of the centroid of the sum of the output membership functions that are activated according to the rules one of the blocks of FIG. 9 and FIG. 10, for example block 902 in the aforementioned exemplary case that the input class is 1 and the sensitivity class is high. Analogously the first weight LUT circuitry 2130 captures the relationship between the value of the Input_Normalized signal output by the division circuitry 2116 and the value of sum of the integrals of the activated output membership functions according to the rules one of the blocks of FIG. 9 and FIG. 10, for example block 902 in the aforementioned exemplary case that the input class is 1 and the sensitivity class is high. As will be described below in further detail each input for which the $(i, j)^{th}$ pixel is in a non-zero sensitivity zone will generate a centroid and a weight and these will be processed to produce an overall centroid for the $(i, j)^{th}$ pixel which is the value of the $(i, j)^{th}$ pixel.

A data output 2132 of the first centroid LUT circuitry 2126 is coupled to a first centroid input 2134 of Multiply and Accumulate (MAC) circuitry 2136. A data output 2138 of the first weight LUT circuitry 2130 is coupled to a first weight input 2140 of the MAC circuitry 2134. Analogous to the first centroid LUT circuitry 2126, the FPGA 2100 also includes $K^{th}$ centroid LUT circuitry 2142 and an $N^{th}$ centroid LUT circuitry 2144. Analogously to the first weight LUT circuitry 2130 the FPGA 2100 also includes $K^{th}$ weight LUT circuitry 2146 and $N^{th}$ weight LUT circuitry 2148. A data output 2150 of the $K^{th}$ centroid LUT circuitry 2142 is coupled to a $K^{th}$ centroid input 2152 of the MAC circuitry 2136. A data output 2154 of the $K^{th}$ weight LUT circuitry 2146 is coupled to a $K^{th}$ weight input 2156 of the MAC circuitry 2136. Similarly, a data output 2158 of $N^{th}$ centroid LUT circuitry 2144 is coupled to a $N^{th}$ centroid input 2160 of the MAC circuitry 2136 and a data output 2162 of the $N^{th}$ weight LUT 2148 is coupled to an $N^{th}$ weight input 2164 of the MAC circuitry 2136. Alternatively, in lieu of any of the centroid LUT circuitries 2126, 2142, 2144 and the weight LUT circuitries 2130 2146, 2148 another type of 1-D function circuitry can be used. 1-D function circuitry receives an input signal representing an independent variable (e.g., capacitance) and in response thereto produces an output signal representing a dependent variable (e.g., indication of a dielectric constant). The 1-D function circuitry can for example comprise a programmed microprocessor or Application Specific Integrated Circuit (ASIC) circuitry. According to a further embodiment the functions of the normalizer circuitry is subsumed into the centroid LUTs 2126, 2142, 2144 and weight LUTs 2130, 2146, 2148 that the normalizer circuitry is coupled into and no separate normalizer circuitry is provided.

The MAC circuitry 2136 produces an output signal which is the result of the dot product of the centroids received at centroid inputs 2134, 2152, 2160 and the weights received at weight inputs 2140, 2156, 2164. As discussed above each centroid and its associated weight represents the output of a set of fuzzy rules that are activated by a particular Input_Normalized value. The operation of the MAC circuitry is described by expression 4 below:

$$\sum_{k \ni \text{Sensitivity}(i,j,k) \neq 0} weight_k(\text{Input\_Normalized}(k)) \cdot \quad \text{EQU. 4}$$

$$Centroid_k(\text{Input\_Normalized}(k))$$

where, k in equation 1 takes on any value for which the Sensitivity(i, j, k) is non-zero and does not stand for the specific input 2008;

$weight_k$(Input_Normalized(k)) is the sum of the integrals of the activated output fuzzy membership functions which are activated in response the Input_Normalized(k) input;

$Centroid_k$(Input_Normalized(k)) is the centroid of sum of the activate fuzzy membership functions activated in response to the Input_Normalized(k) input; and the summation is taken over all values of k such that the Sensitivity(i,j,k) class is nonzero.

An output 2166 of the MAC circuitry 2136 is coupled to a numerator input 2168 of divider circuitry 2170.

The outputs 2138, 2154, 2162 of the weight LUTs 2130, 2146, 2148 are also coupled to a set of summand signal inputs 2172 of summing circuitry 2174 which sums weights included in data signals received from the weight LUTs 2130, 2146, 2148 and generates a sum signal at an output 2176. The output 2176 of the summing circuitry 2174 is coupled to a denominator input 2178 of the divider circuitry 2170. A quotient output of the divider circuitry 2170 outputs the $(i, j)^{th}$ pixel value 2180. The output is described by equation 5.

$$Pixel(i, j) = \frac{\Sigma_{k \ni \text{Sensitivity}(i,j,k) \neq 0} weight_k(\text{Input\_Normalized}(k)) \cdot Centroid_k(\text{Input\_Normalized}(k))}{\Sigma_{k \ni \text{Sensitivity}(i,j,k) \neq 0} weight_k(\text{Input\_Normalized}(k))} \quad \text{EQU. 5}$$

where Pixel(i, j) is the $(i, j)^{th}$ pixel value.

Evaluation of equation 5 by the MAC circuitry 2136, the summing circuitry 2174 and the divider circuitry 2170 is a process of defuzzification of the partially defuzzified information born in the signals produced by the associated pairs of the centroid LUT circuitry 2126, 2142, 2144 and weight LUT circuitry 2130, 2146, 2148.

A person of ordinary skill in the art can use a hardware description language to configure a commercial FPGA according to the schematic shown in FIG. 21.

FIG. 22 is a side view of an ECT sensor head 2200 that has multiple axially spaced rings of sensing electrodes 2202, 2204, 2206, 2208 including a first ring of sensing electrodes 2202, a second ring of sensing electrodes 2204, a third ring of sensing electrodes 2206, and a fourth ring of sensing electrodes 2208. Each ring of sensing electrodes includes individual sensing electrodes 2210 (only three of which are numbered to avoid crowding the drawing). The ECT sensor head 2200 is arranged around a chemical processing vessel 2212 which holds a heterogeneous dielectric material. A space within the processing vessel 2212 is virtually divided into a 3-D array of voxels (as opposed to a 2-D array of pixels in the embodiments described above). In preparation for operating the ECT sensor head, 3-D sensitivity maps analogous to the 2-D sensitivity maps shown FIGS. 7A-7F can be obtained by measurement or numerical electrostatic simulation. According to one embodiment mutual capacitance measurements are restricted to being between sensing electrodes 2208 in a common ring. According to another example, mutual capacitance measurements between sensing electrodes in different rings are also included. To the extent that the algorithm and systems for fuzzy logic, dielectric ECT imaging described above image each pixel independently of other pixels, it will be appreciated that the same algorithms and systems can be extended to imaging a 3-D volume and used to process the mutual capacitance readings from the ECT sensor head 2200 in order to estimate a dielectric constant for each voxel. The ECT reader 108 can wirelessly communicate with the ECT sensor head 2200, receive the mutual capacitance readings, and perform fuzzy logic image synthesis to produce a 3-D image of the heterogeneous dielectric material in the processing vessel 2212. 3-D rendering methods that use a level of transparency for enclosing, or foreground dielectric materials can be used in the ECT reader to display 3-D images obtained from the ECT sensor head 2200.

In certain embodiments an overall confidence estimate for a ECT imaging system can be determined based on a first error term that is dependent on a number of elements used in a Finite Element Method (FEM) calculation that is used in an ECT imaging system or to provide data (e.g., sensitivity data) for use in the ECT imaging system and a second error term that is associated with a noise in the mutual capacitance measurements that are made by the ECT imaging system. The overall confidence estimate can be obtained from the first term and the second term using type-2 fuzzy logic.

Table I below summarizes a set of fuzzy rules that may be used to obtain the overall confidence estimate from the capacitance measurement noise and the number of FEM elements. In table I, each row represents a fuzzy logic conditional (IF..THEN) relation. The first two columns of table I specify input membership functions appearing in the antecedents of the fuzzy logic conditional relations and the last column specifies an output membership function for the fuzzy logic conditional relation. The first column identifies input membership functions for different levels of capacitance noise, i.e., LOW, MEDIUM and HIGH. The second column identifies input membership functions for different numbers of FEM elements, i.e., LOW, MEDIUM and HIGH.

TABLE I

| Input 1 (Noise) Representing uncertainty of the capacitance measurements Normalized (0-1) | Input 2 (# of elements) Representing uncertainty of the FEM Normalized (0-1) | Output (Level of Confidence) (0-100) |
|---|---|---|
| LOW | LOW | MEDIUM |
| LOW | MEDIUM | HIGH |
| LOW | HIGH | VERY-HIGH |
| MEDIUM | LOW | LOW |
| MEDIUM | MEDIUM | MEDIUM |
| MEDIUM | HIGH | HIGH |
| HIGH | LOW | VERY-LOW |
| HIGH | MEDIUM | LOW |
| HIGH | HIGH | MEDIUM |

Table I encodes fuzzy logic conditional statements of the form:

IF (condition on noise AND condition on number of FEM elements) THEN confidence is specified output level.

By way of example, the first row of data of table I encodes the fuzzy logic conditional statement IF (noise=LOW AND number of FEM elements=LOW) THEN Confidence=MEDIUM.

FIG. 23 is a graph 2300 including plots of type-2 fuzzy logic membership functions 2302, 2304, 2306, 2308, 2310, 2312 including a low noise membership function 2302, 2304, a medium noise membership function 2306, 2308 and a high noise membership function 2310, 2312. The low noise input membership function 2302, 2304 includes a low noise lower bound 2302 and a low noise upper bound 2304. Similarly, the medium noise input membership function 2306, 2308 includes a medium noise lower bound 2304 and a medium noise upper bound 2306; and the high noise input membership function 2310, 2312 includes a high noise lower bound 2310 and a high noise upper bound 2312. Type-2 input fuzzy membership functions have an upper bound and a lower bound that reflects uncertainty in their input values.

FIG. 24 is a graph 2400 including plots of type-2 fuzzy logic membership functions 2402, 2404, 2406, 2408, 2410, 2412 including a low FEM element count membership function 2402, 2404, a medium FEM element count membership function 2406, 2408 and a high FEM element count membership function 2410, 2412. The low FEM element count membership function 2402, 2404 includes a low element count lower bound 2402 and a low element count upper bound 2404. Similarly, the medium FEM element count membership function 2406, 2408 includes a medium FEM element count lower bound 2406 and a medium FEM element count upper bound 2408; and the high FEM element count membership function 2410, 2412 includes a high FEM element count lower bound 2410 and a high FEM element count upper bound 2412.

FIG. 23 includes input membership function corresponding to one part of the antecedent of the fuzzy logic conditional statements that are represented in table I, in particular FIG. 23 includes input membership functions for noise which is the first column of table I. FIG. 24 includes input membership functions corresponding to a second part of the antecedent of the fuzzy logic conditional statements represented in table I, in particular the number of FEM elements which is the second column of table I.

As stated above the first row of data of table I encodes the fuzzy logic conditional statement IF (noise=LOW AND number of FEM elements=LOW) THEN Confidence=MEDIUM. FIG. 23 and FIG. 24 are marked up to show evaluation of this rule. An input value of noise is labeled X1 on the abscissa of graph 2300 in FIG. 23. A vertical line 2314 is drawn from the input value of X1 up through the low noise lower bound 2302 and the low noise upper bound 2304. A lower horizontal line 2316 is drawn from the intersection of the vertical line 2314 and the low noise lower bound 2302 and a higher horizontal line 2318 is drawn from the intersection of the vertical line 2314 and the low noise upper bound 2314. The two horizontal lines 2316, 2318 represent two bounds on the activation level of the low noise membership function 2302, 2304 due to the input value of X1.

The graph 2400 shown in FIG. 24 shows the evaluation of the second part of the fuzzy rule antecedent FEM elements=LOW. A vertical line 2414 extends from an input number of FEM elements X2 through the low element count lower bound 2402 and the low element count upper bound 2404. A lower horizontal line 2416 extends from the intersection of the vertical line 2414 and the low element count lower bound 2402 and an upper horizontal line 2418 extends from the intersection of the vertical line 2414 and the low element count upper bound 2404. The two horizontal lines 2416, 2418 represent two bounds on the activation level of the low number of FEM elements membership function 2402, 2404 due to the input value of X2. Because the antecedent of the fuzzy logic conditional statement uses an AND operator to connect the degree of membership signified by noise=LOW and the degree of membership signified by FEM elements=LOW the result of the AND operation is to select the lessor degree of membership which in the case illustrated in FIGS. 23-24 with inputs X1 and X2 is the degree of membership of the input X1 in the LOW noise membership function 2302, 2304. Consequently, the degree of membership represented by lower horizontal line 2316 and upper horizontal line 2318 is transferred to the output membership function 2506 (FIG. 25) of the consequent of the fuzzy rule IF (noise=LOW AND number of FEM elements=LOW) THEN Confidence=MEDIUM which is MEDIUM.

FIG. 25 is a graph including type-2 fuzzy logic output membership functions 2502, 2504, 2506, 2408, 2510 including a VERY LOW 2502, LOW 2504, MEDIUM 2506, HIGH 2508 and VERY HIGH 2510. These output membership functions 2402, 2504, 2506, 2508, 2510 are specified for each type-2 fuzzy logic rule in the third row of Table 1. FIG. 25 specifically illustrates activation of the MEDIUM output membership function 2506 as part of the rule IF (noise=LOW AND number of FEM elements=LOW) THEN Confidence=MEDIUM. As discussed above the antecedent of this rule is illustrated with reference to FIGS. 23-24. As shown in FIG. 25 the level of the lower horizontal line 2316 and the upper horizontal line 2318 has been transferred to the MEDIUM output membership function 2506 to establish a range of activation of the MEDIUM output membership function 2506. Defuzzification of the output membership function in combination with the defuzzification of other output membership functions is described hereinbelow.

Analogous to FIGS. 23-25 which illustrate execution of the type-2 fuzzy logic rule IF (noise=LOW AND number of FEM elements=LOW) THEN Confidence=MEDIUM which is specified in the first row table I, FIGS. 26-28 illustrate execution of the type-2 fuzzy logic rule IF (noise=LOW AND number of FEM elements=MEDIUM) THEN Confidence=HIGH which is specified in the second row of table I. In FIG. 27, a lower horizontal line 2716 and an upper horizontal line 2718 represent the degree of activation of the MEDIUM input membership function 2406, 2408 in response to the input X2. Because the result of the AND operation is to select the lessor the degrees of membership the levels of the lower horizontal line 2716 and the upper horizontal line chosen over the degrees of membership 2316, 2318 associated with the low capacitance noise input membership function 2302, 2304 and are transferred to the HIGH output membership function 2408 as shown in FIG. 28.

Proceeding along with the example illustrated in FIGS. 23-28, FIG. 29 is a graph showing the VERY LOW 2502, LOW 2504, MEDIUM 2506, HIGH 2508 and VERY HIGH 2510 output membership functions. The MEDIUM output membership function 2506 is marked with the lower horizontal line 2316 and the upper horizontal line 2318 indicating the activation by the fuzzy rule IF (noise=LOW AND number of FEM elements=LOW) THEN Confidence=MEDIUM that is described above with reference to FIGS. 23-25. Similarly, the HIGH output membership function 2506 is marked with the lower horizontal line 2716 and the upper horizontal line 2718 indicating the activation by the fuzzy rule IF (noise=LOW AND number of FEM elements=MEDIUM) THEN Confidence=HIGH that is illustrated in FIGS. 26-28.

Figure 30:
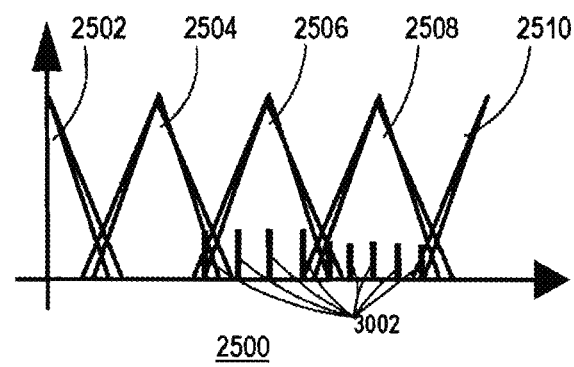
FIG. 30 illustrates a process of defuzzifying output membership functions that are output by two conditional fuzzy logic rules, which are illustrated with reference to FIGS. 23-28 according to one example.

In the first stage of defuzzification the vertical centroid of the activated output membership function is calculated at a set fixed points. In the case that the activated type-2 output membership functions are constant valued between their lower bounds and upper bounds, the vertical centroids are simply the median or average between the lower bound and the upper bound at each point. FIG. 30 shows a sequence of sample values 3002 representing the vertical centroid values. Other calculation methods for the defuzzification of type-2 fuzzy sets can be used as well.

Figure 31:
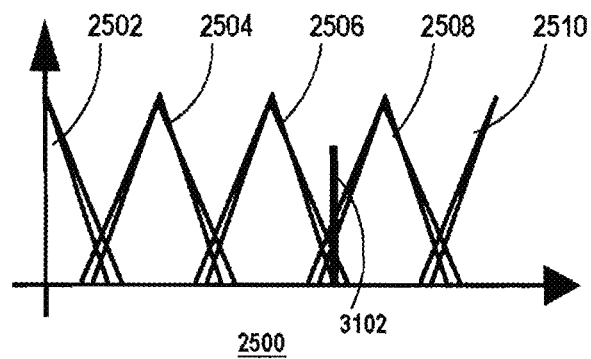
FIG. 31 illustrates a process of defuzzifying output membership functions that are output by two conditional fuzzy logic rules, which are illustrated with reference to FIGS. 23-28 according to one example.

In the second stage of defuzzification a horizontal centroid of the samples 2902 representing the vertical centroid values is calculated. In FIG. 31 the horizontal centroid is indicated by a thick horizontal line 3102. The horizontal centroid 3102 represents the confidence level in the output of an ECT imaging system.

In the case that there are multiple activations of the same output membership function, for example two activations of the MEDIUM output membership function including one from: IF (noise=LOW AND number of FEM elements=LOW) THEN Confidence=MEDIUM and one from: IF (noise=MEDIUM AND number of FEM elements=MEDIUM) THEN Confidence=MEDIUM, an aggregation process using MAX operator is carried out in which the maximum upper and lower membership degrees are chosen for each point in the output membership function MEDIUM.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. An electrical capacitance tomography (ECT) system comprising:
   a plurality of ECT sensor heads, each ECT sensor head including:

a plurality of electrodes disposed about a measurement region, first circuitry configured to measure mutual capacitance between a plurality of pairs of electrodes of the plurality of electrodes and obtain a plurality of mutual capacitance measurements, and a first wireless transceiver coupled to the first circuitry and configured to transmit the plurality of mutual capacitance measurements; and an ECT reader including:

a second wireless transceiver configured to selectively communicate with each of the ECT sensor heads to receive the plurality of mutual capacitance measurements, and second circuitry including a fuzzy logic image synthesizer configured to process the received plurality of mutual capacitance measurements and produce an image corresponding to contents included in the measurement region.

2. The ECT system according to claim 1, wherein the fuzzy logic image synthesizer of the ECT reader is included in a field programmable gate array.

3. The ECT system according to claim 2, wherein the ECT reader includes a battery coupled to the field programmable gate array.

4. The ECT system according to claim 2, wherein the ECT reader further includes:

a display driver coupled to the fuzzy logic image synthesizer, and a display coupled to the display driver and configured to display the image corresponding to the contents included in the measurement region.

5. The ECT system according to claim 1, wherein the plurality of electrodes are arranged in a ring fashion around the measurement region.

6. The ECT system according to claim 1, wherein the set of electrodes includes a plurality of rings of electrodes.

7. The ECT system according to claim 1 wherein the fuzzy logic image synthesizer is configured to:

for each particular location among a plurality of locations in the measurement region and for each $K^{TH}$ mutual capacitance measurement of at least a subset of more than one of the plurality of mutual capacitance measurements:

evaluate at least a subset of a plurality of fuzzy rules wherein each fuzzy rule includes an antecedent that depends on a degree of membership of the $K^{TH}$ mutual capacitance measurement in an input fuzzy membership function that is related to a magnitude of capacitance, and a consequent that includes an output membership function that is related to a magnitude of a dielectric constant, defuzzify the output membership function of the at least subset of the plurality of fuzzy rules to obtain an indication of the dielectric at the particular location based on each $K^{TH}$ mutual capacitance measurement, and defuzzify the indications of dielectric at the particular location obtained from all of the $K^{TH}$ mutual capacitance measurements in the subset of the plurality of mutual capacitance measurements to obtain a value for a dielectric constant at the particular location.

8. The ECT system according to claim 7, wherein the first or second circuitry is configured to normalize the plurality of mutual capacitance measurements prior to evaluating the plurality of fuzzy rules.

9. The ECT system according to claim 8, wherein the first or second circuitry is configured to normalize the plurality of mutual capacitance measurements such that each of a set of normalized mutual capacitance measurements is described by:

$$\text{Input\_Normalized}(k) = \frac{(\text{Input\_Value}(k) - \text{CAP\_LOW}(L, M))}{(\text{CAP\_HIGH}(L, M) - \text{CAP\_LOW}(L, M))}$$

where, L is an index identifying a first electrode,

M is an index identifying a second electrode, k is an integer index that corresponds to a particular combination of L and M values, Input_Normalized(k) is a normalized mutual capacitance measured between an $L^{TH}$ sensing electrode and an $M^{TH}$ sensing electrode, CAP_LOW(L, M) is a mutual capacitance measured between an $L^{TH}$ sensing electrode and an $M^{TH}$ sensing electrode when all of a set of pixels defined in the measurement domain are filled with a preselected low dielectric constant material, and CAP_HIGH(L, M) is a mutual capacitance measured between an $L^{TH}$ sensing electrode and an $M^{TH}$ sensing electrode when all of the pixels are filled with a preselected high dielectric constant material.

10. The ECT system according to claim 7, wherein for each particular pair of electrodes among the plurality of pairs of electrodes, a plurality of sensitivity zones are defined based on a sensitivity of a particular mutual capacitance measurement between the particular pair of electrodes to changes in a dielectric constant at each particular position in the measurement domain, and each of the at least subset of the plurality of fuzzy rules for each particular location in the measurement domain is selected based on which of the plurality of sensitivity zones corresponds to the particular location.

11. The ECT system according to claim 1, wherein the second circuitry includes:

a plurality of inputs for receiving signals based on the plurality of mutual capacitance measurements, and for at least one subregion of the measurement region of at least one of the plurality of ECT sensor heads:

a plurality of Look Up Tables (LUT) circuitry each of which includes:

an address input coupled to one of a subset that includes more than one of the plurality of inputs, and a data output; and additional circuitry that is coupled to the data output of the plurality of LUT circuitry and configured to operate on data received from the data output of the plurality of LUT circuitry and to produce an image value for the at least one region therefrom.

12. The ECT system according to claim 11, wherein the plurality of LUT circuitry includes:

a plurality of centroid LUT circuitry each of which includes a centroid LUT address input and a centroid LUT data output; and a plurality of weight LUT circuitry each of which includes a weight LUT address input and a weight LUT data output, wherein each of the plurality of weight LUT circuitry is configured to output, at the weight LUT data output, a weight associated with a centroid that is output by the corresponding one of the plurality of centroid LUTs.

13. The ECT system according to claim 12, wherein each weight LUT circuitry and the corresponding one of the plurality of centroid LUT circuitry implements the relationship between an input to a set of fuzzy rules and a defuzzified output of the set of fuzzy rules.

14. The ECT system according to claim 12, wherein the additional circuitry includes:
   MAC circuitry including:
      a plurality of centroid inputs each of which is coupled to the centroid LUT data output of one of the plurality of centroid LUT circuitries;
      a plurality of weight inputs each of which is coupled to the weight LUT data output of one of the plurality of weight LUT circuitries; and
      a MAC circuitry output.

15. The ECT system according to claim 14, wherein the additional circuitry further includes:
   summing circuitry including:
      a plurality of weight inputs each of which is coupled to the weight LUT data output of one of the plurality of weight LUT circuitries; and
      a summing circuitry output;
      wherein the summing circuitry is configured to sum the plurality of corresponding weight values that are received at the plurality of weight inputs of the summing circuitry, and output a result of the sum at the summing circuitry output.

16. The ECT system according to claim 15, wherein the additional circuitry further includes:
   divider circuitry including:
      a numerator input coupled to the MAC circuitry output;
      a denominator input coupled to the summing circuitry output; and
      an divider circuitry output;
      wherein the divider circuitry is configured to output, at the divider circuitry output, a resulting quotient as a function of the numerator and denominator which is the image value for the at least one region.

17. The ECT system according to claim 16, wherein:
   each weight LUT circuitry and the corresponding one of the plurality of centroid LUT circuitry implements the relationship between an input to a set of fuzzy rules and a defuzzified output of the set of fuzzy rules; and
   the MAC circuitry, the summing circuitry, and the divider circuitry constitute a defuzzifier that serves to defuzzify output from the plurality of centroid LUT circuitries and the plurality of weight LUT circuitries.

18. The ECT system according to claim 11, further comprising:
   normalizer circuitry interposed between the plurality of inputs and the plurality of LUT circuitry.

19. The ECT system according to claim 18, wherein the normalizer circuitries includes:
   subtraction circuitry including:
      a first operand input coupled to one of the subset of more than one of the plurality of inputs;
      a second operand input coupled to a first constant value memory; and
      a subtraction circuitry result output;
   division circuitry including:
      a first argument input coupled to the subtraction circuitry result output;
      a second argument input coupled to a second constant value memory; and
      a division circuitry result output that serves as a normalizer circuitry output and is coupled to the address input of one of the plurality of LUT circuitries.

20. The ECT system according to claim 11, wherein the second circuitry is implemented in a field-programmable gate array (FPGA).

21. An electrical capacitance tomography (ECT) method comprising:
   at each of a plurality of ECT sensor heads, each ECT sensor head including a plurality of electrodes disposed about a measurement region, first circuitry and a first wireless receiver coupled to the first circuitry,
      measuring, via the first circuitry, mutual capacitance between a plurality of pairs of electrodes of the plurality of electrodes to obtain a plurality of mutual capacitance measurements;
   transmitting, via the first wireless transceiver, the plurality of mutual capacitance measurements to an ECT reader;
   receiving, at a second wireless transceiver of the ECT reader configured to selectively communicate with the ECT sensor head, the plurality of mutual capacitance measurements;
   processing, via second circuitry including a fuzzy logic image synthesizer, the received plurality of mutual capacitance measurements; and
   producing an image corresponding to contents included in the measurement region.

22. An electrical capacitance tomography reader (ECT) reader including:
   a wireless transceiver configured to selectively communicate with each of a plurality of ECT sensor heads and receive a plurality of mutual capacitance measurements, the plurality of mutual capacitance measurements being obtained based on a measurement of mutual capacitance between a plurality of pairs of electrodes of a plurality of electrodes disposed about a measurement region, the plurality of electrodes being part of one or more the ECT sensor heads; and
   circuitry including a fuzzy logic image synthesizer configured to process the received plurality of mutual capacitance measurements and produce an image corresponding to contents included in the measurement region.

* * * * *